US007994176B2

(12) United States Patent
Li et al.

(10) Patent No.: US 7,994,176 B2
(45) Date of Patent: Aug. 9, 2011

(54) INHIBITORS OF 11-BETA-HYDROXYSTEROID DEHYDROGENASE 1

(75) Inventors: Renhua Li, Fishers, IN (US); Thomas Edward Mabry, Indianapolis, IN (US); Owen Brendan Wallace, Westfield, IN (US); Leonard Larry Winneroski, Jr., Greenwood, IN (US); Yanping Xu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 436 days.

(21) Appl. No.: 12/297,964

(22) PCT Filed: Apr. 24, 2007

(86) PCT No.: PCT/US2007/067296
§ 371 (c)(1),
(2), (4) Date: Oct. 21, 2008

(87) PCT Pub. No.: WO2007/127726
PCT Pub. Date: Nov. 8, 2007

(65) Prior Publication Data
US 2009/0099182 A1    Apr. 16, 2009

Related U.S. Application Data

(60) Provisional application No. 60/745,569, filed on Apr. 25, 2006.

(51) Int. Cl.
*A61K 31/496* (2006.01)
*A61K 31/454* (2006.01)
*C07D 403/02* (2006.01)
*C07D 401/14* (2006.01)
*C07D 401/04* (2006.01)
*C07D 207/26* (2006.01)

(52) U.S. Cl. .................. 514/254.01; 514/316; 544/372; 546/187; 546/208; 548/543

(58) Field of Classification Search .............. 514/235.5, 514/254.01, 316, 326, 424; 544/372, 141; 546/187, 208; 548/543
See application file for complete search history.

(56) References Cited

U.S. PATENT DOCUMENTS

| 2008/0207691 | A1 | 8/2008 | Aicher et al. |
| 2008/0214621 | A1 | 9/2008 | Aicher et al. |
| 2008/0275043 | A1 | 11/2008 | Aicher et al. |
| 2009/0069326 | A1 | 3/2009 | Allen et al. |
| 2009/0088428 | A1 | 4/2009 | Saeed et al. |
| 2009/0088430 | A1 | 4/2009 | Wallace et al. |
| 2009/0099180 | A1 | 4/2009 | Mabry et al. |
| 2009/0111800 | A1 | 4/2009 | Aicher et al. |
| 2009/0111809 | A1 | 4/2009 | Bush et al. |
| 2009/0156571 | A1 | 6/2009 | Aicher et al. |
| 2009/0239911 | A1 | 9/2009 | Wallace et al. |
| 2009/0264650 | A1 | 10/2009 | Yamashita et al. |
| 2009/0275613 | A1 | 11/2009 | Li et al. |

FOREIGN PATENT DOCUMENTS

| EP | 1864971 | 12/2007 |
| WO | WO 2004/056744 | 7/2004 |
| WO | WO 2005/108360 | 11/2005 |
| WO | WO 2005/108361 | 11/2005 |
| WO | WO 2006/040329 | 4/2006 |
| WO | WO 2006/049952 | 5/2006 |
| WO | WO 2006/053024 | 5/2006 |
| WO | WO 2006/068991 | 6/2006 |
| WO | WO 2006/068992 | 6/2006 |
| WO | WO 2006/104280 | 10/2006 |
| WO | WO 2007/084314 | 7/2007 |
| WO | WO 2007/124254 | 11/2007 |
| WO | WO 2007/124329 | 11/2007 |
| WO | WO 2007/124337 | 11/2007 |
| WO | WO 2007/127688 | 11/2007 |
| WO | WO 2007/127693 | 11/2007 |
| WO | WO 2007/127704 | 11/2007 |
| WO | WO 2007/127763 | 11/2007 |
| WO | WO 2007/127765 | 11/2007 |
| WO | WO 2007/127901 | 11/2007 |
| WO | WO 2008/157752 | 12/2008 |

OTHER PUBLICATIONS

Yeh et al.: Discovery of orally active butyrolactam 11 β-HSD1 inhibitors, Bioorganic & Medicinal Chemistry Letters, Nov. 1, 2006, 16(21), pp. 5555-5560.
Schuster, Daniela et al.: The Discovery of New 11β-Hydroxysteroid Dehydrogenase Type 1 Inhibitors by Common Feature Pharmacophore Modeling and Virtual Screening, J. Medicinal Chemistry, 2006, 49, pp. 3454-3466.
Konno et al.: Electrolytic Partial Fluorination of Organic Compounds. 6. Highly Regioselective Eletrochemical Monofluorination of Aliphatic Nitrogen-Containing Heterocycles, Tetrahedron Letters, 1992, vol. 33, No. 46, pp. 7017-7020.

*Primary Examiner* — Kamal Saeed
*Assistant Examiner* — Kristin Bianchi
(74) *Attorney, Agent, or Firm* — Dan L. Wood

(57) ABSTRACT

The present invention discloses novel compounds of Formula I: having 11 Beta-HSD type 1 antagonist activity, as well as methods for preparing such compounds. In another embodiment, the invention discloses pharmaceutical compositions comprising compounds of Formula I, as well as methods of using the compounds and compositions to treat diabetes, hyperglycemia, obesity, hypertension, hyperlipidemia, metabolic syndrome, and other conditions associated with 11 Beta-HSD type 1 activity. X-17377

21 Claims, No Drawings

INHIBITORS OF 11-BETA-HYDROXYSTEROID DEHYDROGENASE 1

This is the national phase application, under 35 USC 371, for PCT/US2007/067296, filed Apr. 24, 2007, which claims the benefit, under 35 USC 119(e), of US provisional application 60/745,569 filed Apr. 25, 2006.

This invention relates to compounds that are inhibitors of 11-β-hydroxysteroid dehydrogenase type 1 ("11-β-HSD1"), and to pharmaceutical compositions thereof, and the uses of these compounds and compositions in the treatment of the human or animal body, and to novel intermediates useful in preparation of the inhibitors. The present compounds show potent and selective inhibition of 11-β-HSD1, and as such are useful in the treatment of disorders responsive to the modulation of 11-β-HSD1, such as diabetes, metabolic syndrome, cognitive disorders, and the like.

Glucocorticoids acting in the liver, adipose tissue, and muscle, are important regulators of glucose, lipid, and protein metabolism. Chronic glucocorticoid excess is associated with insulin resistance, visceral obesity, hypertension, and dyslipidemia, which also represent the classical hallmarks of metabolic syndrome. 11-β-HSD1 catalyses the conversion of inactive cortisone to active cortisol, and has been implicated in the development of metabolic syndrome. Evidence in rodents and humans links 11-β-HSD1 to metabolic syndrome. Evidence suggests that a drug which specifically inhibits 11-β-HSD1 in type 2 diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secretion from the beta cells of the islet may also be increased. Evidence from animal and human studies also indicates that an excess of glucocorticoids impair cognitive function. Recent results indicate that inactivation of 11-β-HSD1 enhances memory function in both men and mice. The 11-β-HSD inhibitor carbenoxolone was shown to improve cognitive function in healthy elderly men and type 2 diabetics, and inactivation of the 11-β-HSD1 gene prevented aging-induced impairment in mice. Selective inhibition of 11-β-HSD1 with a pharmaceutical agent has recently been shown to improve memory retention in mice.

A number of publications have appeared in recent years reporting agents that inhibit 11-β-HSD1. See International Application WO2004/056744 which discloses adamantyl acetamides as inhibitors of 11-β-HSD, International Application WO2005/108360 which discloses pyrrolidin-2-one and piperidin-2-one derivatives as inhibitors of 11-β-HSD, and International Application WO2005/108361 which discloses adamantyl pyrrolidin-2-one derivatives as inhibitors of 11-β-HSD. In spite of the number of treatments for diseases that involve 11-β-HSD1, the current therapies suffer from one or more inadequacies, including poor or incomplete efficacy, unacceptable side effects, and contraindications for certain patient populations. Thus, there remains a need for an improved treatment using alternative or improved pharmaceutical agents that inhibit 11-β-HSD1 and treat the diseases that could benefit from 11-β-HSD1 inhibition. The present invention provides such a contribution to the art based on the finding that a novel class of compounds has a potent and selective inhibitory activity on 11-β-HSD1. The present invention is distinct in the particular structures and their activities. There is a continuing need for new methods of treating diabetes, metabolic syndrome, and cognitive disorders, and it is an object of this invention to meet these and other needs.

The present invention provides a compound structurally represented by formula I:

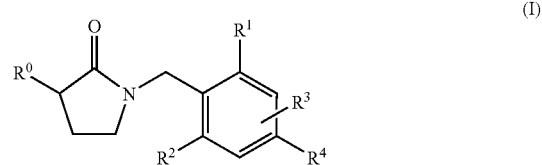

or a pharmaceutically acceptable salt thereof, wherein $R^0$ is

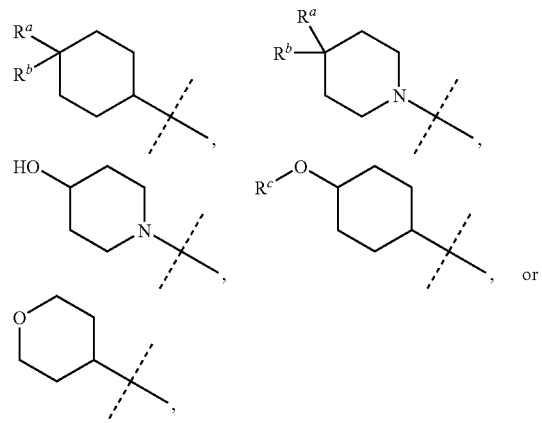

wherein the dashed line represents the point of attachment to the $R^0$ position in formula I; wherein $R^a$ is —H or -halogen; $R^b$ is —H or halogen; $R^c$ is —H, —CH$_3$ or —CH$_2$—CH$_3$;

$R^1$ is —H, -halogen, —O—CH$_3$ (optionally substituted with one to three halogens), or —CH$_3$ (optionally substituted with one to three halogens);

$R^2$ is —H, -halogen, —O—CH$_3$ (optionally substituted with one to three halogens), or —CH$_3$ (optionally substituted with one to three halogens);

$R^3$ is —H or -halogen;

$R^4$ is
—OH, -halogen, -cyano, —(C$_1$-C$_4$)alkyl(optionally substituted with one to three halogens), —(C$_1$-C$_6$)alkoxy (optionally substituted with one to three halogens), —SCF$_3$, —C(O)O(C$_1$-C$_4$)alkyl, —O—CH$_2$—C(O)NH$_2$, —(C$_3$-C$_8$)cycloalkyl, —O-phenyl-C(O)O—(C$_1$-C$_4$)alkyl, —CH$_2$-phenyl, —NHSO$_2$—(C$_1$-C$_4$)alkyl, —NHSO$_2$-phenyl(R$^{21}$)(R$^{21}$), —(C$_1$-C$_4$)alkyl-C(O)N(R$^{10}$)(R$^{11}$),

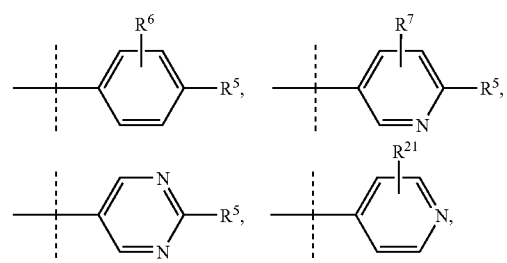

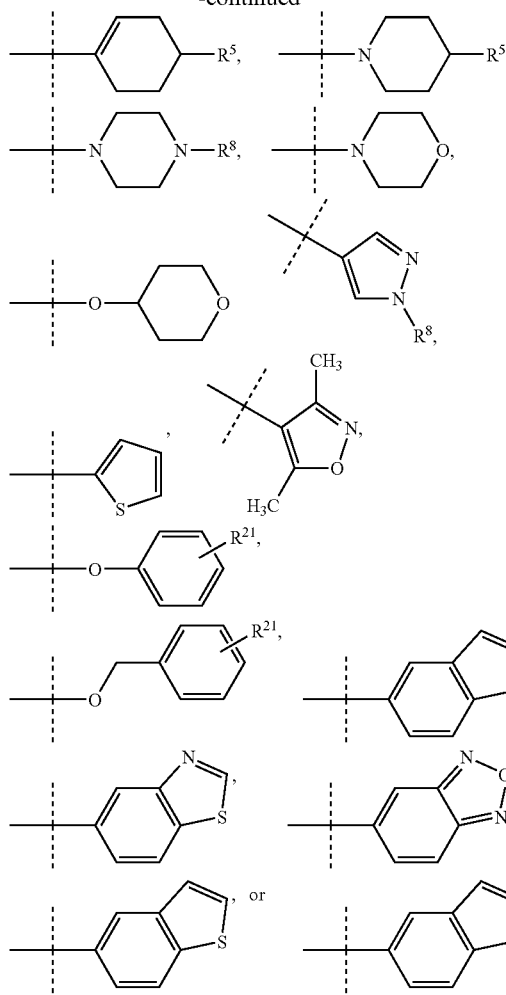

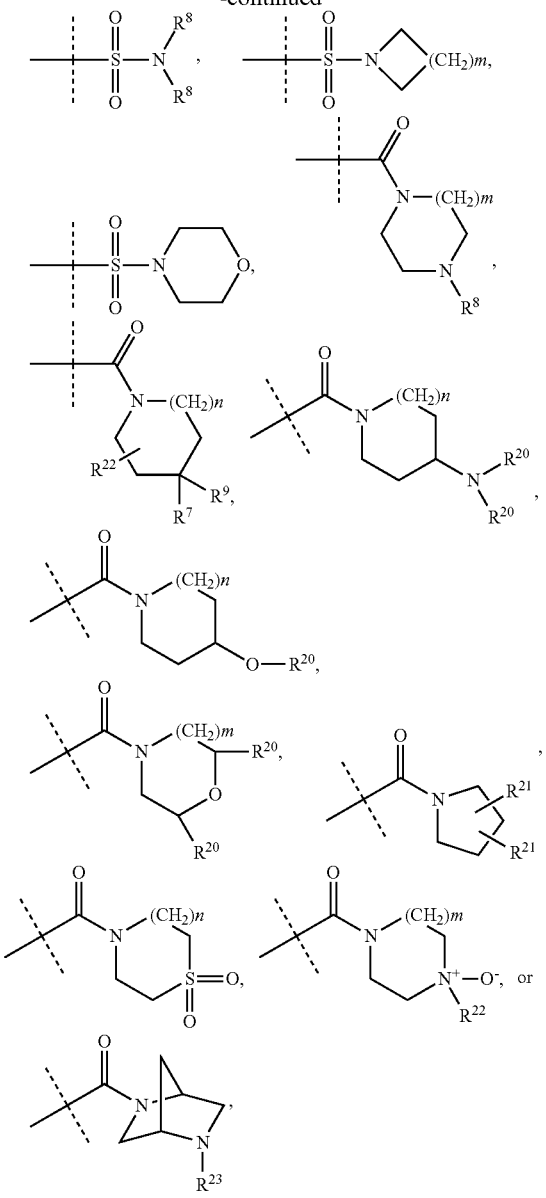

wherein the dashed line represents the point of attachment to the $R^4$ position in formula I;

$R^5$ is
—H, -halogen, —OH, —CN, —$(C_1$-$C_4)$alkyl(optionally substituted with 1 to 3 halogens), —C(O)OH, —C(O)O—$(C_1$-$C_4)$alkyl, —C(O)—$(C_1$-$C_4)$alkyl, —O—$(C_1$-$C_4)$alkyl(optionally substituted with 1 to 3 halogens), —$SO_2$—$(C_1$-$C_4)$alkyl, —$N(R^8)(R^8)$, -phenyl$(R^{21})$$(R^{21})$, —C(O)—NH—$(C_3$-$C_6)$cycloalkyl,

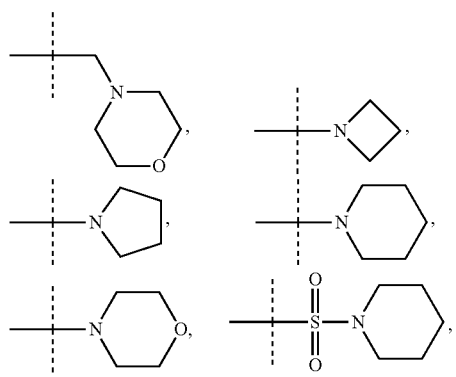

wherein the dashed line represents the point of attachment to the position indicated by $R^5$;

wherein m is 1, 2, or 3;

wherein n is 0, 1, or 2, and wherein when n is 0, then "$(CH_2)n$" is a bond;

$R^6$ is
—H, -halogen, —CN, or —$(C_1$-$C_4)$alkyl(optionally substituted with 1 to 3 halogens);

$R^7$ is
—H, -halogen, or —$(C_1$-$C_4)$alkyl(optionally substituted with 1 to 3 halogens);

$R^8$ is independently at each occurrence —H or —$(C_1$-$C_6)$alkyl(optionally substituted with 1 to 3 halogens);

$R^9$ is —H or -halogen;

$R^{10}$ and $R^{11}$ are each independently
—H or —$(C_1$-$C_4)$alkyl, or $R^{10}$ and $R^{11}$ taken together with the nitrogen to which they are attached form piperidinyl, piperazinyl, or pyrrolidinyl;

$R^{20}$ is independently at each occurrence —H, or —$(C_1$-$C_3)$alkyl(optionally substituted with 1 to 3 halogens);

$R^{21}$ is independently at each occurrence —H, -halogen, or —($C_1$-$C_3$)alkyl(optionally substituted with 1 to 3 halogens);

$R^{22}$ is independently at each occurrence —H or —($C_1$-$C_6$)alkyl(optionally substituted with 1 to 3 halogens); and $R^{23}$ is independently at each occurrence —H, —($C_1$-$C_4$)alkyl (optionally substituted with 1 to 3 halogens), or —C(O)O—($C_1$-$C_4$)alkyl.

The present invention provides compounds of formula I that are useful as potent and selective inhibition of 11-β-HSD1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

In one embodiment, the present invention provides compounds of Formula I or a pharmaceutically acceptable salt thereof as described in detail above. While all of the compounds of the present invention are useful, certain of the compounds are particularly interesting and are preferred. The following listings set out several groups of preferred compounds.

In another embodiment the invention provides a compound structurally represented by formula I, or a pharmaceutically acceptable salt thereof, wherein $R^0$ is

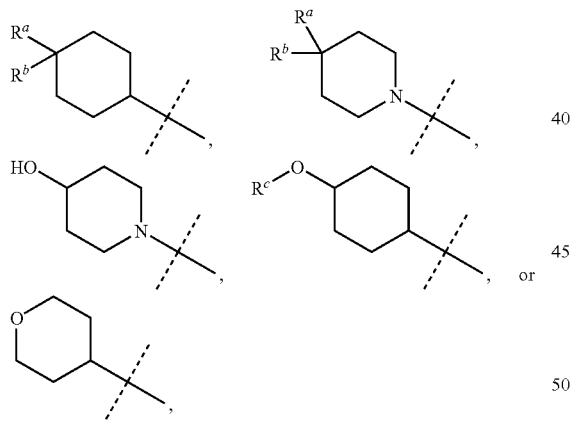

wherein the dashed line represents the point of attachment to the $R^0$ position in formula I; wherein $R^a$ is -halogen; $R^b$ is —H or halogen; $R^c$ is —H, —$CH_3$ or —$CH_2$—$CH_3$;

$R^1$ is -halogen; $R^2$ is -halogen; $R^3$ is —H or -halogen;

$R^4$ is
—OH, -halogen, -cyano, —($C_1$-$C_4$)alkyl(optionally substituted with one to three halogens), —($C_1$-$C_6$)alkoxy (optionally substituted with one to three halogens), —$SCF_3$, —C(O)O($C_1$-$C_4$)alkyl, —O—$CH_2$—C(O)$NH_2$, —($C_3$-$C_8$)cycloalkyl, —O-phenyl-C(O)O—($C_1$-$C_4$)alkyl, —$CH_2$-phenyl, —$NHSO_2$—($C_1$-$C_4$)alkyl, —$NHSO_2$-phenyl($R^{21}$)($R^{21}$), —($C_1$-$C_4$)alkyl-C(O)N($R^{10}$)($R^{11}$),

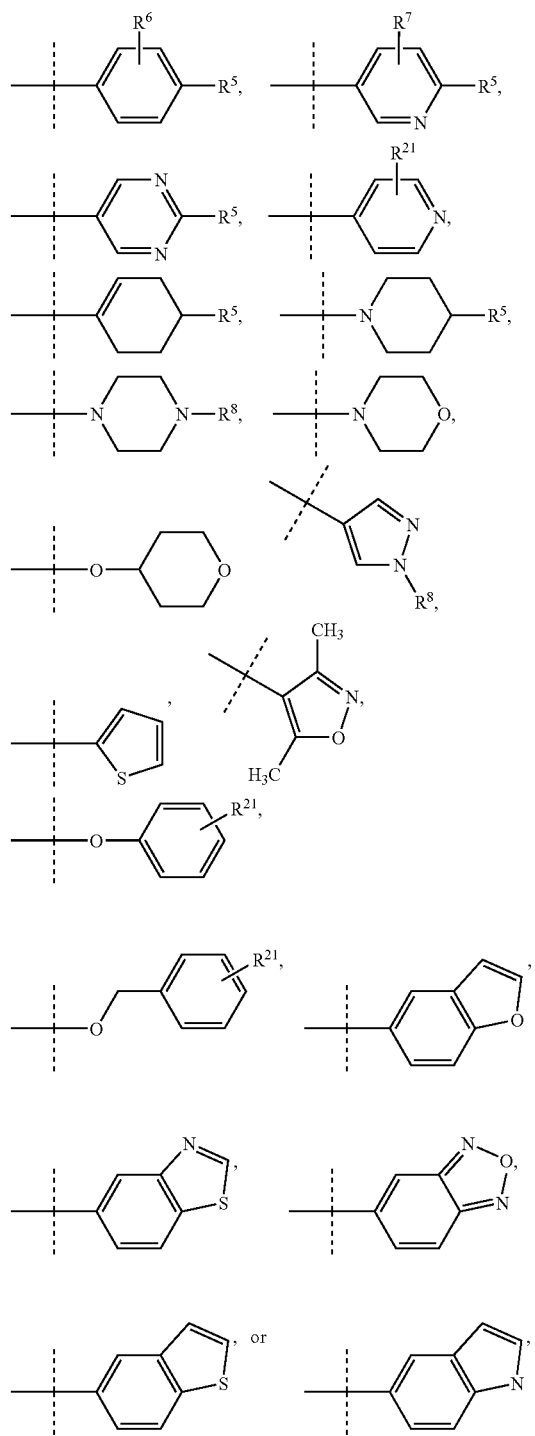

wherein the dashed line represents the point of attachment to the $R^4$ position in formula I;

$R^5$ is
—H, -halogen, —OH, —CN, —($C_1$-$C_4$)alkyl(optionally substituted with 1 to 3 halogens), —C(O)OH, —C(O)O—($C_1$-$C_4$)alkyl, —C(O)—($C_1$-$C_4$)alkyl, —O—($C_1$-$C_4$)alkyl(optionally substituted with 1 to 3 halogens), —$SO_2$—($C_1$-$C_4$)alkyl, —N($R^8$)($R^8$), -phenyl($R^{21}$)($R^{21}$), —C(O)—NH—($C_3$-$C_6$)cycloalkyl,

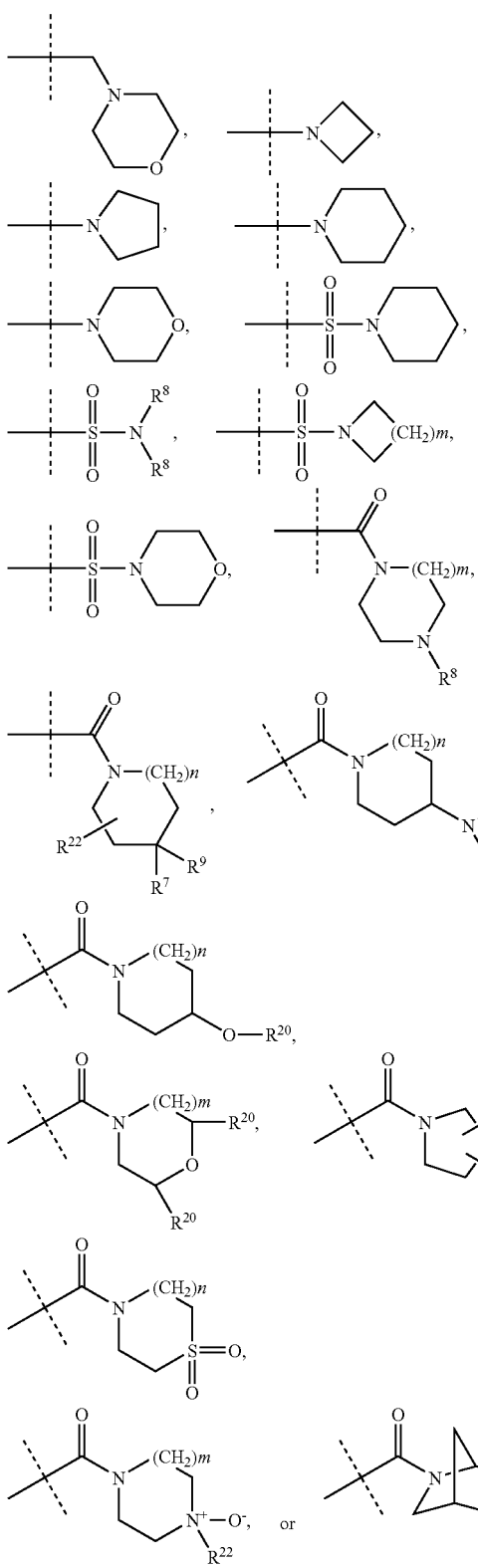

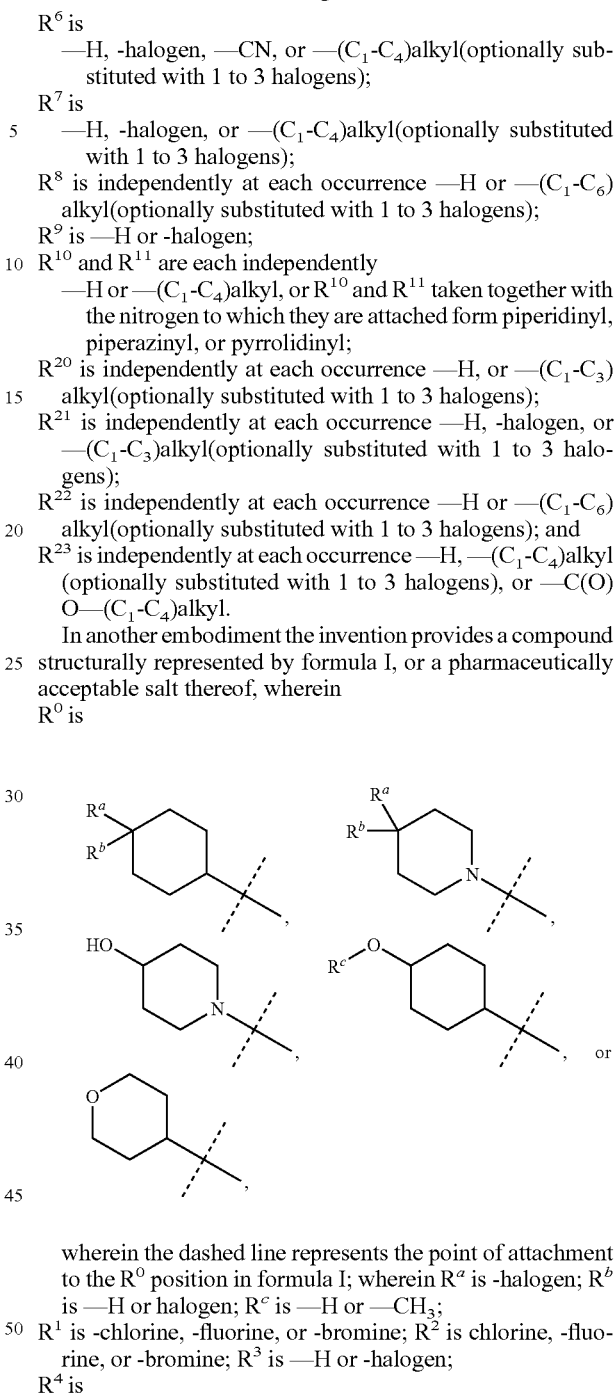

wherein the dashed line represents the point of attachment to the position indicated by $R^5$;

wherein m is 1, 2, or 3;

wherein n is 0, 1, or 2, and wherein when n is 0, then "$(CH_2)n$" is a bond;

$R^6$ is
—H, -halogen, —CN, or —$(C_1$-$C_4)$alkyl(optionally substituted with 1 to 3 halogens);

$R^7$ is
—H, -halogen, or —$(C_1$-$C_4)$alkyl(optionally substituted with 1 to 3 halogens);

$R^8$ is independently at each occurrence —H or —$(C_1$-$C_6)$alkyl(optionally substituted with 1 to 3 halogens);

$R^9$ is —H or -halogen;

$R^{10}$ and $R^{11}$ are each independently
—H or —$(C_1$-$C_4)$alkyl, or $R^{10}$ and $R^{11}$ taken together with the nitrogen to which they are attached form piperidinyl, piperazinyl, or pyrrolidinyl;

$R^{20}$ is independently at each occurrence —H, or —$(C_1$-$C_3)$alkyl(optionally substituted with 1 to 3 halogens);

$R^{21}$ is independently at each occurrence —H, -halogen, or —$(C_1$-$C_3)$alkyl(optionally substituted with 1 to 3 halogens);

$R^{22}$ is independently at each occurrence —H or —$(C_1$-$C_6)$alkyl(optionally substituted with 1 to 3 halogens); and $R^{23}$ is independently at each occurrence —H, —$(C_1$-$C_4)$alkyl (optionally substituted with 1 to 3 halogens), or —C(O)O—$(C_1$-$C_4)$alkyl.

In another embodiment the invention provides a compound structurally represented by formula I, or a pharmaceutically acceptable salt thereof, wherein $R^0$ is wherein the dashed line represents the point of attachment to the $R^0$ position in formula I; wherein $R^a$ is -halogen; $R^b$ is —H or halogen; $R^c$ is —H or —$CH_3$;

$R^1$ is -chlorine, -fluorine, or -bromine; $R^2$ is chlorine, -fluorine, or -bromine; $R^3$ is —H or -halogen;

$R^4$ is

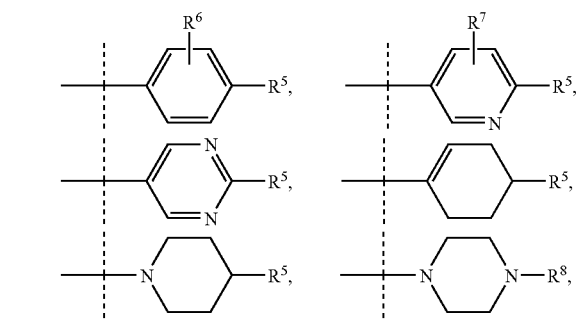

wherein the dashed line represents the point of attachment to the $R^4$ position in formula I;

$R^5$ is
- —H, -halogen, —OH, —CN, —($C_1$-$C_4$)alkyl(optionally substituted with 1 to 3 halogens), —C(O)OH, —C(O)O—($C_1$-$C_4$)alkyl, —C(O)—($C_1$-$C_4$)alkyl,
- —O—($C_1$-$C_4$)alkyl(optionally substituted with 1 to 3 halogens), —$SO_2$—($C_1$-$C_4$)alkyl, —N($R^8$)($R^8$), -phenyl($R^{21}$)($R^{21}$), —C(O)—NH—($C_3$-$C_6$)cycloalkyl, wherein the dashed line represents the point of attachment to the position indicated by $R^5$; wherein m is 1, 2, or 3;

$R^6$ is
- —H, -halogen, —CN, or —($C_1$-$C_4$)alkyl(optionally substituted with 1 to 3 halogens);

$R^7$ is
- —H, -halogen, or —($C_1$-$C_4$)alkyl(optionally substituted with 1 to 3 halogens);

$R^8$ is independently at each occurrence —H or —($C_1$-$C_6$)alkyl(optionally substituted with 1 to 3 halogens);

$R^9$ is —H or -halogen;

$R^{20}$ is independently at each occurrence —H, or —($C_1$-$C_3$)alkyl(optionally substituted with 1 to 3 halogens);

$R^{21}$ is independently at each occurrence —H, -halogen, or —($C_1$-$C_3$)alkyl(optionally substituted with 1 to 3 halogens);

$R^{22}$ is independently at each occurrence —H or —($C_1$-$C_6$)alkyl(optionally substituted with 1 to 3 halogens);

$R^{23}$ is independently at each occurrence —H, —($C_1$-$C_4$)alkyl (optionally substituted with 1 to 3 halogens), or —C(O)O—($C_1$-$C_4$)alkyl.

In another embodiment the invention provides a compound structurally represented by formula I, or a pharmaceutically acceptable salt thereof, wherein
$R^0$ is

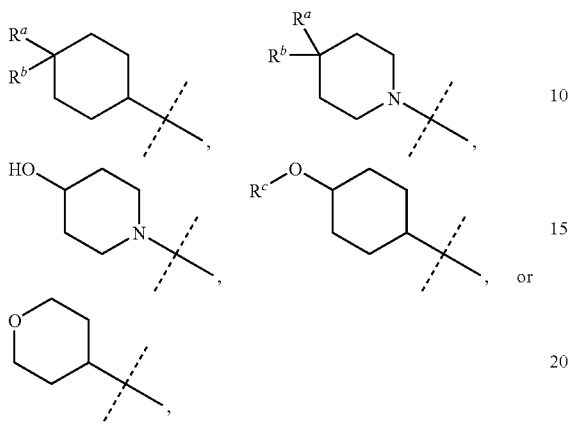

wherein the dashed line represents the point of attachment to the $R^0$ position in formula I; wherein $R^a$ is -halogen; $R^b$ is —H or halogen; $R^c$ is —H or —CH$_3$;

$R^1$ is -chlorine, -fluorine, or -bromine; $R^2$ is chlorine, -fluorine, or -bromine; $R^3$ is —H or -halogen;

$R^4$ is

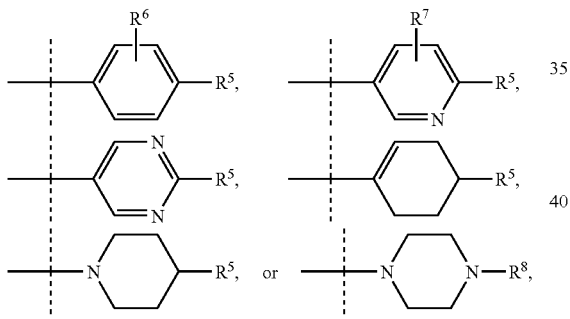

wherein the dashed line represents the point of attachment to the $R^4$ position in formula I;

$R^5$ is
—H, -halogen, —(C$_1$-C$_4$)alkyl(optionally substituted with 1 to 3 halogens), —C(O)OH, —C(O)O—(C$_1$-C$_4$)alkyl, —C(O)—(C$_1$-C$_4$)alkyl, —O—(C$_1$-C$_4$)alkyl(optionally substituted with 1 to 3 halogens), —SO$_2$—(C$_1$-C$_4$)alkyl, —N(R$^8$)(R$^8$),

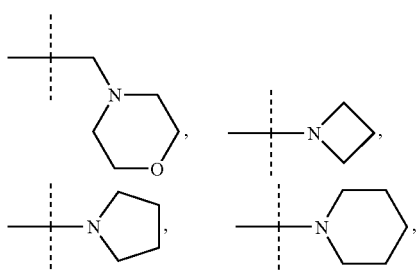

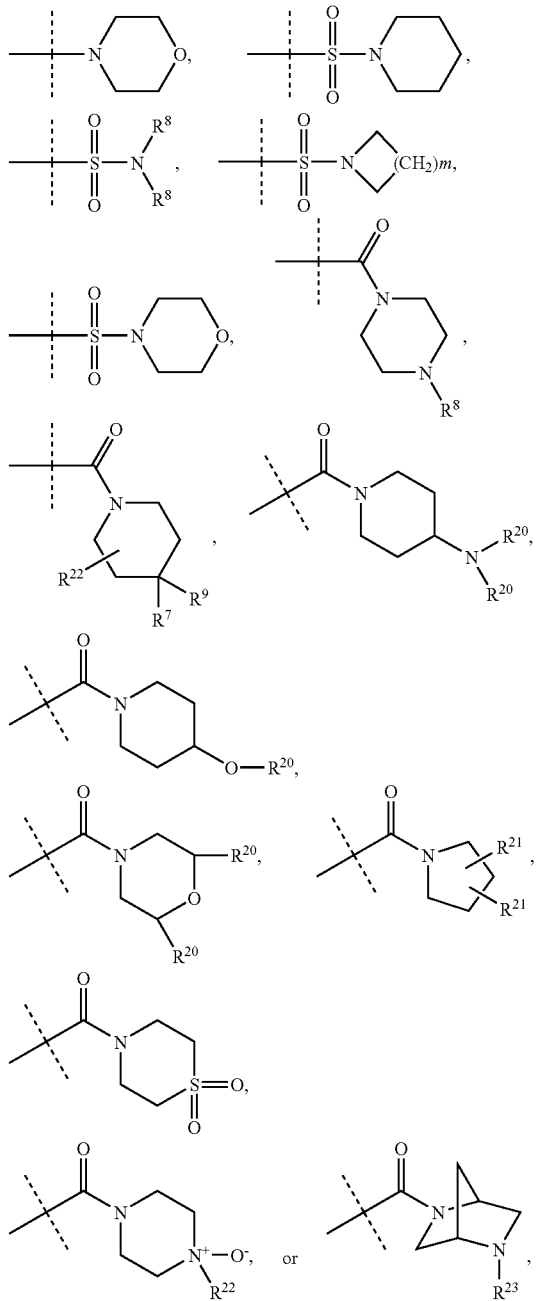

wherein the dashed line represents the point of attachment to the position indicated by $R^5$; wherein m is 1, 2, or 3;

$R^6$ is
—H, -halogen, —CN, or —(C$_1$-C$_4$)alkyl(optionally substituted with 1 to 3 halogens);

$R^7$ is
—H, -halogen, or —(C$_1$-C$_4$)alkyl(optionally substituted with 1 to 3 halogens);

$R^8$ is independently at each occurrence —H or —(C$_1$-C$_6$)alkyl(optionally substituted with 1 to 3 halogens);

$R^9$ is —H or -halogen;

$R^{20}$ is independently at each occurrence —H, or —(C$_1$-C$_3$)alkyl(optionally substituted with 1 to 3 halogens);

$R^{21}$ is independently at each occurrence —H, -halogen, or —($C_1$-$C_3$)alkyl(optionally substituted with 1 to 3 halogens);
$R^{22}$ is independently at each occurrence —H or —($C_1$-$C_6$) alkyl(optionally substituted with 1 to 3 halogens); and
$R^{23}$ is independently at each occurrence —H, —($C_1$-$C_4$)alkyl (optionally substituted with 1 to 3 halogens), or —C(O)O—($C_1$-$C_4$)alkyl.

In another embodiment the invention provides a compound structurally represented by formula I, or a pharmaceutically acceptable salt thereof, wherein
$R^0$ is

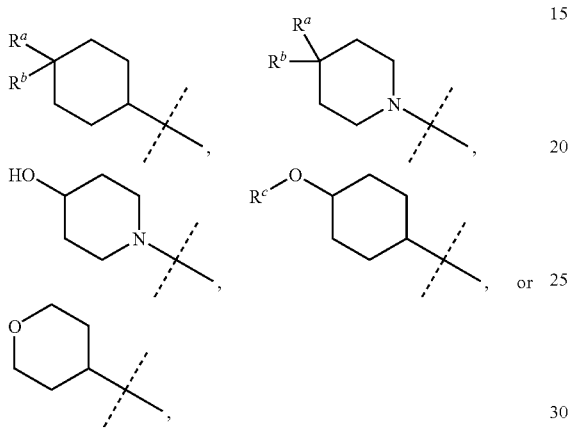

wherein the dashed line represents the point of attachment to the $R^0$ position in formula I; wherein $R^a$ is -halogen; $R^b$ is —H or halogen; $R^c$ is —H or —$CH_3$;
$R^1$ is -chlorine, -fluorine, or -bromine; $R^2$ is chlorine, -fluorine, or -bromine; $R^3$ is —H or -halogen;
$R^4$ is

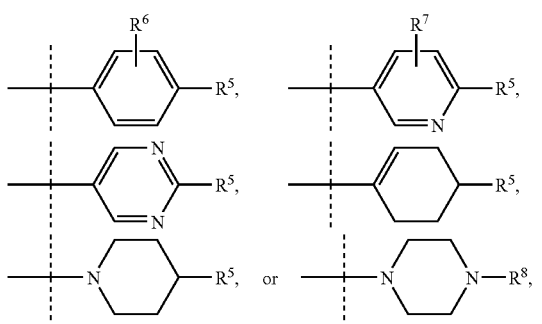

wherein the dashed line represents the point of attachment to the $R^4$ position in formula I;
$R^5$ is

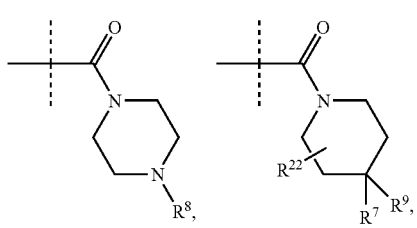

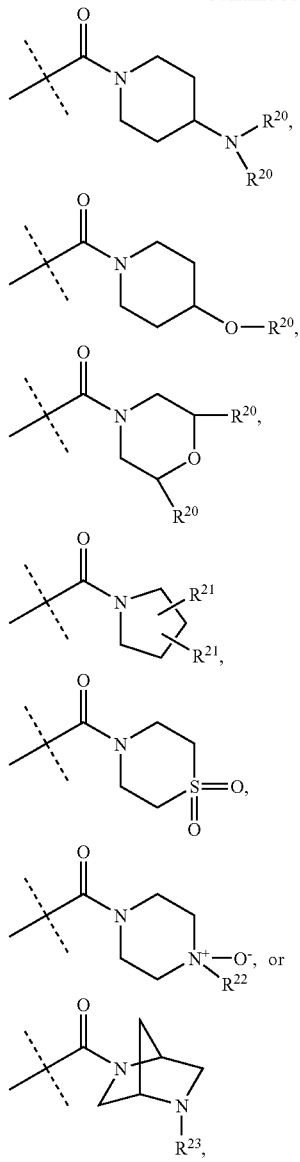

wherein the dashed line represents the point of attachment to the position indicated by $R^5$;
$R^6$ is
—H, -halogen, —CN, or —($C_1$-$C_4$)alkyl(optionally substituted with 1 to 3 halogens);
$R^7$ is
—H, -halogen, or —($C_1$-$C_4$)alkyl(optionally substituted with 1 to 3 halogens);
$R^8$ is independently at each occurrence —H or —($C_1$-$C_6$) alkyl(optionally substituted with 1 to 3 halogens);
$R^9$ is —H or -halogen;
$R^{20}$ is independently at each occurrence —H, or —($C_1$-$C_3$) alkyl(optionally substituted with 1 to 3 halogens);
$R^{21}$ is independently at each occurrence —H, -halogen, or —($C_1$-$C_3$)alkyl(optionally substituted with 1 to 3 halogens);
$R^{22}$ is independently at each occurrence —H or —($C_1$-$C_6$) alkyl(optionally substituted with 1 to 3 halogens); and
$R^{23}$ is independently at each occurrence —H, —($C_1$-$C_4$)alkyl (optionally substituted with 1 to 3 halogens), or —C(O)O—($C_1$-$C_4$)alkyl.

In another embodiment the invention provides a compound structurally represented by formula I, or a pharmaceutically acceptable salt thereof, wherein
$R^0$ is

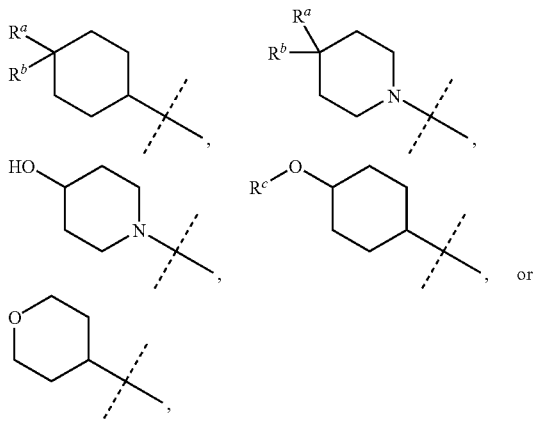

wherein the dashed line represents the point of attachment to the $R^0$ position in formula I; wherein $R^a$ is -halogen; $R^b$ is —H or halogen; $R^c$ is —H or —CH$_3$;
$R^1$ is -chlorine, -fluorine, or -bromine; $R^2$ is chlorine, -fluorine, or -bromine; $R^3$ is —H or -halogen;
$R^4$ is

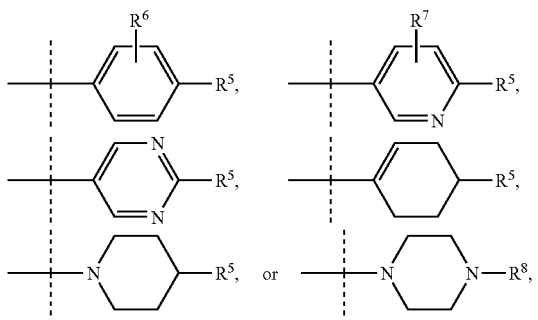

wherein the dashed line represents the point of attachment to the $R^4$ position in formula I;
$R^5$ is
—SO$_2$—(C$_1$-C$_4$)alkyl,

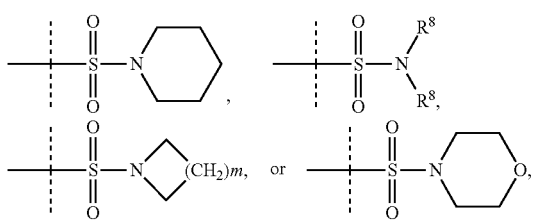

wherein the dashed line represents the point of attachment to the position indicated by $R^5$; wherein m is 1, 2, or 3;
$R^6$ is
—H, -halogen, —CN, or —(C$_1$-C$_4$)alkyl(optionally substituted with 1 to 3 halogens);

$R^7$ is
—H, -halogen, or —(C$_1$-C$_4$)alkyl(optionally substituted with 1 to 3 halogens); and
$R^8$ is independently at each occurrence —H or —(C$_1$-C$_6$) alkyl(optionally substituted with 1 to 3 halogens).

In another embodiment the invention provides a compound structurally represented by formula I, or a pharmaceutically acceptable salt thereof, wherein
$R^0$ is

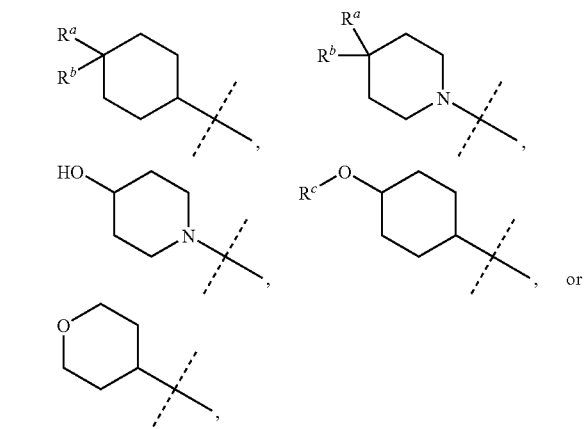

wherein the dashed line represents the point of attachment to the $R^0$ position in formula I; wherein $R^a$ is -halogen; $R^b$ is —H or halogen; $R^c$ is —H or —CH$_3$;
$R^1$ is -chlorine, -fluorine, or -bromine; $R^2$ is chlorine, -fluorine, or -bromine; $R^3$ is —H or -halogen;
$R^4$ is

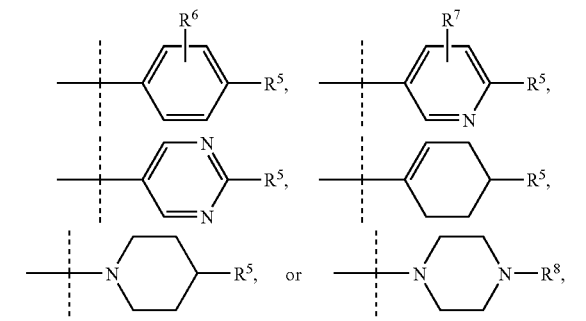

wherein the dashed line represents the point of attachment to the $R^4$ position in formula I;
$R^5$ is
—N(R$^8$)(R$^8$),

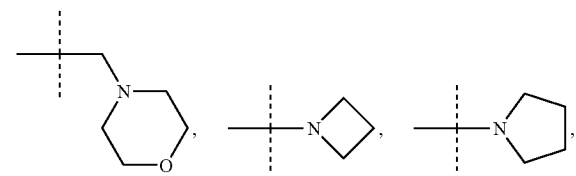

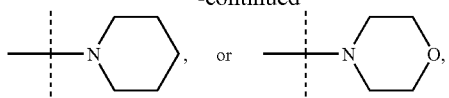

wherein the dashed line represents the point of attachment to the position indicated by $R^5$;

$R^6$ is
—H, -halogen, —CN, or —($C_1$-$C_4$)alkyl(optionally substituted with 1 to 3 halogens);

$R^7$ is
—H, -halogen, or —($C_1$-$C_4$)alkyl(optionally substituted with 1 to 3 halogens); and $R^8$ is independently at each occurrence —H or —($C_1$-$C_6$)alkyl(optionally substituted with 1 to 3 halogens).

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably embodiments of the invention are structurally represented by the formula:

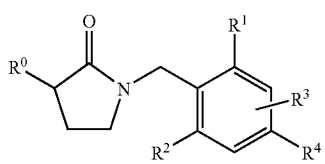

wherein $R^0$ is

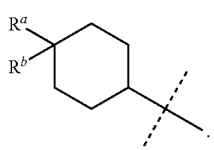

Preferably $R^0$ is

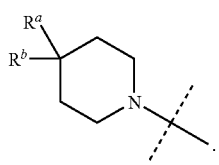

Preferably $R^0$ is

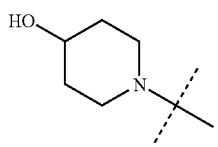

Preferably $R^0$ is

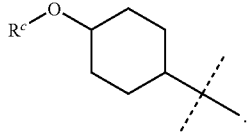

Preferably $R^0$ is

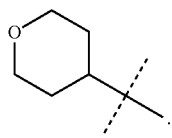

Preferably $R^0$ is

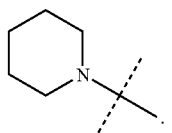

Preferably $R^0$ is

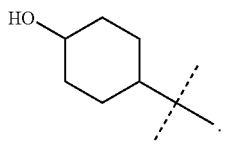

Preferably $R^0$ is

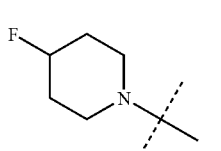 or 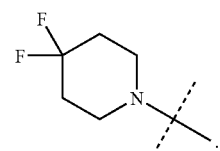

Preferably $R^0$ is

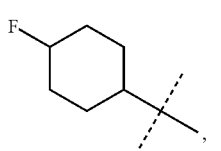, or 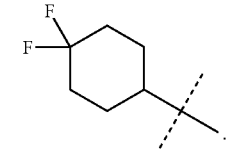

Preferably $R^a$ is -halogen. Preferably $R^a$ is -fluorine. Preferably $R^b$ is halogen. Preferably $R^b$ is -fluorine. Preferably $R^c$ is —H. Preferably $R^c$ is —$CH_3$. Preferably $R^1$ is -halogen. Preferably $R^1$ is —$CH_3$. Preferably $R^1$ is -chlorine, -fluorine, or -bromine. Preferably $R^1$ is chlorine. Preferably $R^1$ is -fluorine. Preferably $R^1$ is -bromine. Preferably $R^2$ is -halogen. Preferably $R^2$ is —$CH_3$. Preferably $R^2$ is chlorine, -fluorine, or -bromine. Preferably $R^2$ is chlorine. Preferably $R^2$ is -fluorine. Preferably $R^2$ is -bromine. Preferably $R^1$ is -chlorine and $R^2$ is chlorine. Preferably $R^3$ is —H. Preferably $R^3$ is -halogen. Preferably $R^1$ is -chlorine and $R^2$ is -chlorine, and $R^3$ is —H.
Preferably $R^4$ is
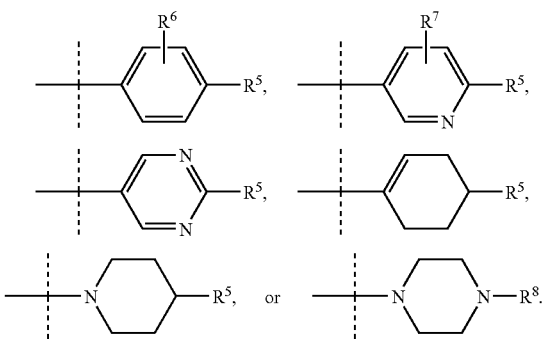
Preferably $R^4$ is
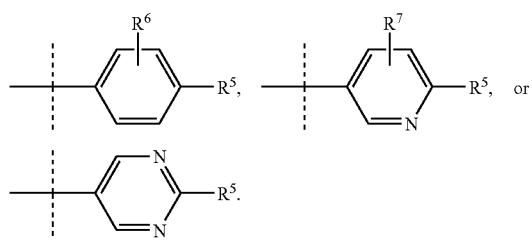
Preferably $R^4$ is
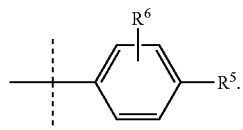
Preferably $R^4$ is
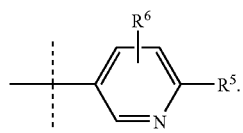
Preferably $R^4$ is
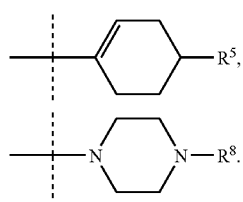
Preferably $R^4$ is
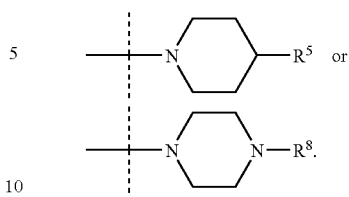
Preferably $R^4$ is
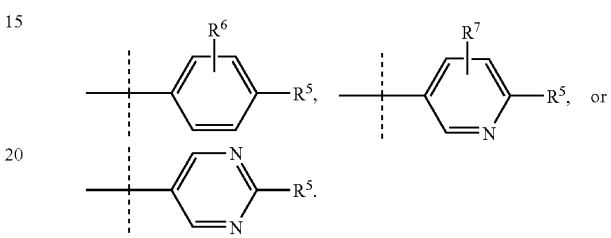
Preferably $R^4$ is
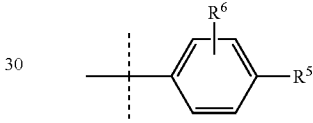
and $R^6$ is —H. Preferably $R^4$ is
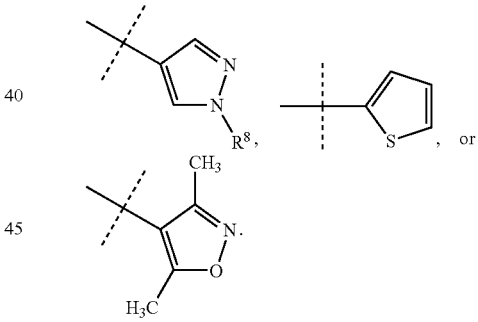
Preferably $R^4$ is
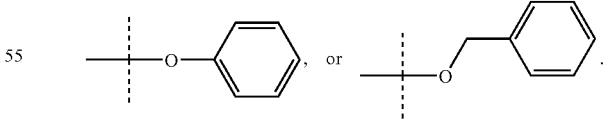
Preferably $R^4$ is
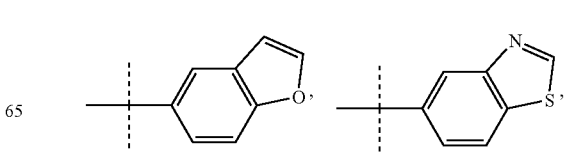

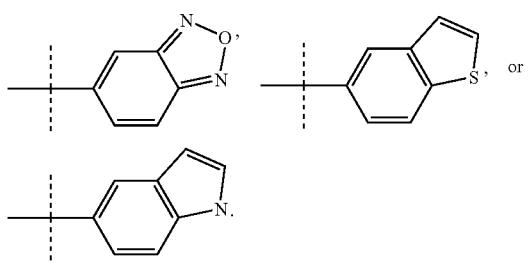
Preferably R⁵ is —N(R⁸)(R⁸),
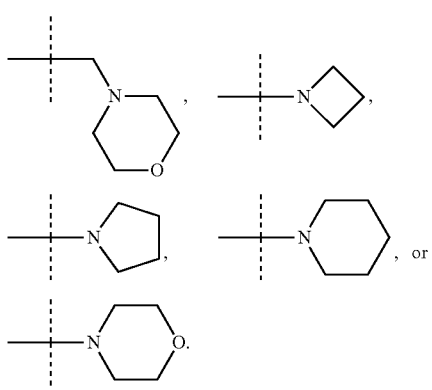
Preferably R⁵ is —SO₂—(C₁-C₄)alkyl,
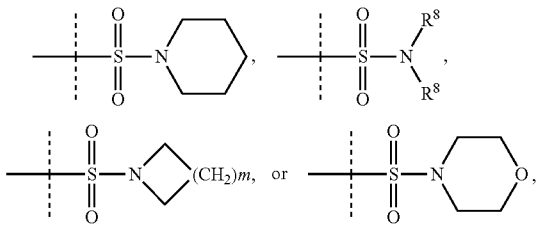
wherein m is 1, 2, or 3.
Preferably R⁵ is
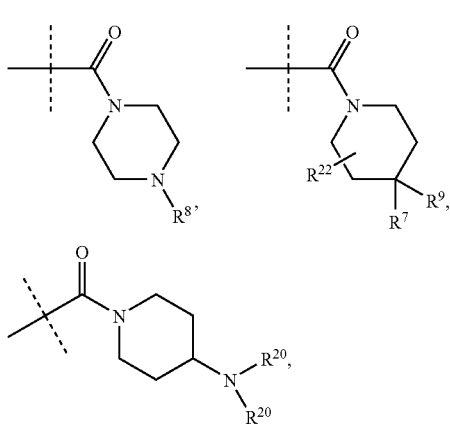
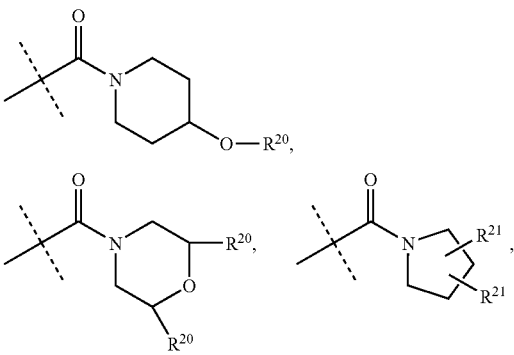
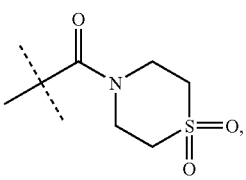
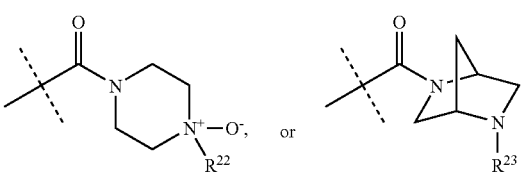
Preferably R⁵ is
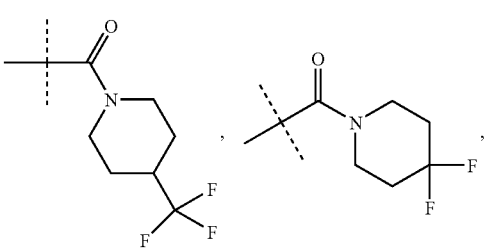
wherein R⁸ is —(C₁-C₃)alkyl (optionally substituted with 1 to 3 halogens), or
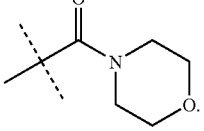

Preferably R⁵ is

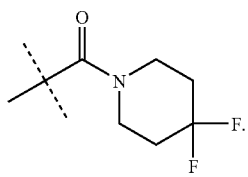

Preferably R⁵ is

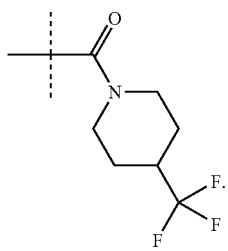

Preferably R⁵

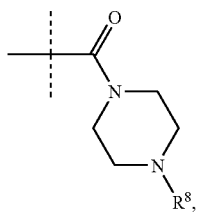

wherein R⁸ is —C₁-C₃)alkyl (optionally substituted with 1 to 3 halogens). Preferably R⁵ is chlorine or fluorine. Preferably R⁶ is —H. Preferably R⁶ is -halogen. Preferably R⁶ is —(C₁-C₄)alkyl(optionally substituted with 1 to 3 halogens). Preferably R⁷ is —H. Preferably R⁷ is -halogen, or —(C₁-C₄)alkyl (optionally substituted with 1 to 3 halogens). Preferably R⁷ is -halogen. Preferably R⁷ is —(C₁-C₄)alkyl(optionally substituted with 1 to 3 halogens). Preferably R⁸ is independently at each occurrence —H. Preferably R⁸ is independently at each occurrence —(C₁-C₃)alkyl. Preferably R⁸ is independently at each occurrence —CH₃. Preferably R⁹ is —H. Preferably R⁹ is -halogen. Preferably R⁷ is -fluorine and R⁹ is -fluorine.

In another embodiment the invention provides a compound structurally represented by formula I, or a pharmaceutically acceptable salt thereof, wherein R⁰ is

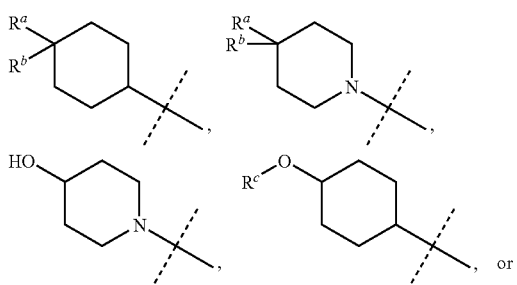

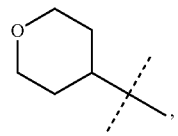

wherein the dashed line represents the point of attachment to the R⁰ position in formula I;
wherein Rᵃ is -halogen; Rᵇ is —H or halogen; Rᶜ is —H or —CH₃;
R¹ is -chlorine; R² is chlorine; R³ is —H;
R⁴ is
-halogen, —OH, —O—CH₃,

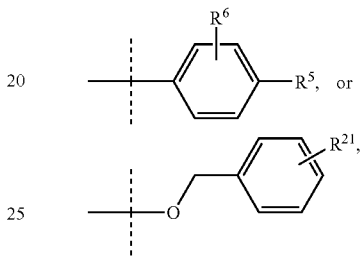

wherein the dashed line represents the point of attachment to the R⁴ position in formula I;
R⁵ is
—H, -chlorine, -fluorine, —CH₃, —CF₃, —C(CH₃)₃, —CH(CH₃)₂, —O—C(CH₃)₂, —C(O)O—CH₃, C(O)OH,

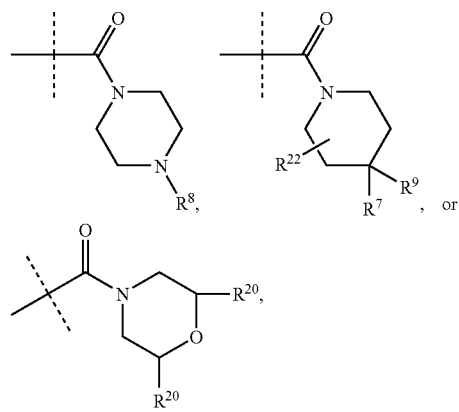

wherein the dashed line represents the point of attachment to the position indicated by R⁵;
R⁶ is —H, -chlorine, -fluorine, -bromine, —CH₃, or —CF₃;
R⁷ is —H, -chlorine, -fluorine, or -bromine;
R⁸ is independently at each occurrence —H or —CH₃, —CH₂—CH₃, —C(CH₃)₃, or —CH(CH₃)₂;
R⁹ is —H or -chlorine, -fluorine, or -bromine;
R²⁰ is independently at each occurrence —H or —CH₃; and
R²² is independently at each occurrence —H.
A preferred embodiment of the invention are compounds of the formula 3-Cyclohexyl-1-{3,5-dichloro-4'-[4-(2-fluoro-ethyl)-piperazine-1-carbonyl]-biphenyl-4-ylmethyl}-pyrrolidin-2-one and 1-[3,5-Dichloro-4'-(4-trifluoromethyl-piperidine-1-carbonyl)-biphenyl-4-ylmethyl]-3-piperidin-1- yl-pyrrolidin-2-one. A further embodiment of the invention are the novel intermediate preparations described herein which are useful for preparing the 11-β-HSD1 inhibitors according to formula I and the embodiments described herein. A further embodiment of the invention are the novel intermediate preparations described herein which are useful for preparing 3-Cyclohexyl-1-{3,5-dichloro-4'-[4-(2-fluoro-ethyl)-piperazine-1-carbonyl]-biphenyl-4-ylmethyl}-pyrrolidin-2-one and 1-[3,5-Dichloro-4'-(4-trifluoromethyl-piperidine-1-carbonyl)-biphenyl-4-ylmethyl]-3-piperidin-1-yl-pyrrolidin-2-one or a pharmaceutically acceptable salt thereof.

Patients with type 2 diabetes often develop "insulin resistance" which results in abnormal glucose homeostasis and hyperglycemia leading to increased morbidity and premature mortality. Abnormal glucose homeostasis is associated with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are important in the management and treatment of diabetes mellitus. Many patients who have insulin resistance but have not developed type 2 diabetes are also at risk of developing "Syndrome X" or "Metabolic syndrome". Metabolic syndrome is characterized by insulin resistance along with abdominal obesity, hyperinsulinemia, high blood pressure, low HDL, high VLDL, hypertension, atherosclerosis, coronary heart disease, and chronic renal failure. These patients are at increased risk of developing the cardiovascular complications listed above whether or not they develop overt diabetes mellitus.

Due to their inhibition of 11-βHSD1, the present compounds are useful in the treatment of a wide range of conditions and disorders in which inhibition of 11-β-HSD1 is beneficial. These disorders and conditions are defined herein as "diabetic disorders" and "metabolic syndrome disorders". One of skill in the art is able to identify "diabetic disorders" and "metabolic syndrome disorders" by the involvement of 11-β-HSD1 activity either in the pathophysiology of the disorder, or in the homeostatic response to the disorder. Thus, the compounds may find use for example to prevent, treat, or alleviate, diseases or conditions or associated symptoms or sequelae, of "Diabetic disorders" and "metabolic syndrome disorders".

"Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, metabolic syndrome, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus the present invention also provides a method of treatment of "Diabetic disorders" and "metabolic syndrome disorders" while reducing and or eliminating one or more of the unwanted side effects associated with the current treatments.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting 11-β-HSD1 activity; for use in inhibiting a 11-β-HSD1 activity mediated cellular response in a mammal; for use in reducing the glycemic level in a mammal; for use in treating a disease arising from excessive 11-β-HSD1 activity; for use in treating diabetic and other metabolic syndrome disorders in a mammal; and for use in treating diabetes, metabolic syndrome, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting 11-β-HSD1 activity; for the manufacture of a medicament for inhibiting 11-β-HSD1 activity mediated cellular response in a mammal; for the manufacture of a medicament for reducing the glycemic level in a mammal; for the manufacture of a medicament for treating a disease arising from excessive 11-β-HSD1 activity; for the manufacture of a medicament for treating diabetic and other metabolic syndrome disorders in a mammal; and for the manufacture of a medicament for preventing or treating diabetes, metabolic syndrome, obesity, hyperglycemia, atherosclerosis, ischemic heart disease, stroke, neuropathy, and improper wound healing.

The present invention further provides a method of treating conditions resulting from excessive 11-β-HSD1 activity in a mammal; a method of inhibiting 11-β-HSD1 activity in a mammal; a method of inhibiting a 11-β-HSD1 activity mediated cellular response in a mammal; a method of reducing the glycemic level in a mammal; a method of treating diabetic and other metabolic syndrome disorders in a mammal; a method of preventing or treating diabetes, metabolic syndrome, obesity, hyperglycemia, atherosclerosis, ischemic heart disease, stroke, neuropathy, and improper wound healing; said methods comprising administering to a mammal in need of such treatment a 11-β-HSD1 activity inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting 11-β-HSD1 activity; adapted for use in inhibiting 11-β-HSD1 activity mediated cellular responses; adapted for use in reducing the glycemic level in a mammal; adapted for use in treating diabetic and other metabolic syndrome disorders in a mammal; and adapted for use in preventing or treating diabetes, metabolic syndrome, obesity, hyperglycemia, atherosclerosis, ischemic heart disease, stroke, neuropathy, and wound healing.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28}$ $Pro^{B28}$ human insulin, EP 368 187 (Aventis), for example Lantus®, GLP-1 and GLP-1 derivatives such as those disclosed in WO 98/08871 (Novo Nordisk A/S), as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S), or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B28}$-tetradecanoyl des (B30) human insulin, $Asp^{B28}$ human insulin, $Lys^{B28}$ $Pro^{B28}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation).

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S).

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

General terms used in the description of compounds herein described bear their usual meanings.

As used herein, the terms "$(C_1-C_3)$alkyl", "$(C_1-C_4)$alkyl" or "$(C_1-C_6)$alkyl" refer to straight-chain or branched-chain saturated aliphatic groups of the indicated number of carbon atoms, such as methyl, ethyl, n-propyl, isopropyl, n-butyl, isobutyl, sec-butyl, t-butyl, and the like. The term "$(C_1-C_6)$ alkoxy" represents a $C_1-C_6$ alkyl group attached through an oxygen and include moieties such as, for example, methoxy, ethoxy, n-propoxy, isopropoxy, and the like. The term "halogen" refers to fluoro, chloro, bromo, and iodo. The term "($C_3$-$C_8$) cycloalkyl" refers to a saturated or partially saturated carbocycle ring of from 3 to 8 carbon atoms, typically 3 to 7 carbon atoms. Examples of ($C_3$-$C_8$) cycloalkyl include but are not limited to cyclopropyl, cyclobutyl, cyclopentyl, cyclohexyl, cycloheptyl, and the like.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

It is understood that guinea pigs, dogs, cats, rats, mice, hamsters, and primates, including humans, are examples of patients within the scope of the meaning of the term "patient". Preferred patients include humans. The term "patient" includes livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may have one or more chiral centers and may exist in a variety of stereoisomeric configurations. As a consequence of these chiral centers the compounds of the present invention can occur as racemates, as individual enantiomers or mixtures of enantiomers, as well as diastereomers and mixtures of diastereomers. All such racemates, enantiomers, diastereomers and mixtures are within the scope of the present invention, whether pure, partially purified, or unpurified mixtures. For the examples provided herein, when a molecule which contains a chiral center or centers of known configuration is presented, its stereochemistry is designated in the name and in the structural representation of the molecule. If the stereochemistry is unknown or undefined its stereochemistry is not designated in the name or in the structural representation of the molecule. Embodiments of the invention include the Examples provided herein, and although the Example provided may be of one chiral or conformational form, or a salt thereof, further embodiments of the invention include all other stereoisomeric and or conformational forms of the examples described, as well as pharmaceutically acceptable salts thereof. These embodiments include any isolated enantiomers, diastereomers, and or conformers of these structures, as well as any mixtures containing more than one form.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms which the compounds are able to form are included within the scope of the present invention.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "psi" refers to pounds per square inch; "TLC" refers to thin layer chromatography; "HPLC" refers to high performance liquid chromatography; "$R_f$" refers to retention factor; "$R_t$" refers to retention time; "δ" refers to part per million downfield from tetramethylsilane; "MS" refers to mass spectrometry, Observed Mass indicates [M+H] unless indicated otherwise. "MS(APCi) refers to atmospheric pressure chemical ionization mass spectrometry, "UV" refers to ultraviolet spectrometry, "$^1$H NMR" refers to proton nuclear magnetic resonance spectrometry. "LCMS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylformamide, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N'-(3-dimethylaminopropyl)carbodiimide hydrochloride, "HOBT" refers to 1-Hydroxy benzotriazole, "Bn-9-BBN" refers to Benzyl-9-borabicyclo[3.3.1]nonane, "Pd(dppf)Cl$_2$" refers to [1,1'-Bis(diphenylphosphino)-ferrocene)dichloropalladium(II), "EDCI" refers to N-Ethyl-N'-(3-dimethylaminopropyl)carbodiimide hydrochloride, "DBU" refers to 1,8-Diazabicyclo[5.4.0]undecene-7, "TBSCl" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$" refers to Bis(dibenzylideneacetone)palladium, "BINAP" refers to 2,2'-Bis(diphenylphospino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi—Pr)$_3$ refers to methyltitanium triisopropoxide, "BBr$_3$" refers to boron tribromide, "PBr$_3$" refers to phosphorous tribromide, "Pd(PPh$_3$)$_4$" refers to tetrakis(triphenylphoshine)palladium (0), "OAc" refers to acetate, "DME" refers to dimethylethane, "Et$_2$O" refers to diethyl ether, "(Ph$_3$P)$_4$Pd" refers to tetrakis (triphenylphoshine)palladium (0), "DMFDMA" refers to N,N-dimethylformamide dimethyl acetal, "Et$_3$N" refers to triethylamine, "tBu" refers to t-butyl, "DIPEA" refers to diisopropylethyl amine, "EDC" refers to -(3-Dimethylaminopropyl)-3-ethylcarbodiimide hydrochloride, "HOAc" refers to acetic acid, "boc" refers to t-butoxycarbonyl. In a structure, "Ph" refers to phenyl, "Me" refers to methyl, "Et" refers to ethyl, "Bn" refers to benzyl, "MeOH" refers to methanol, "OTf" refers to trifluoromethanesulfonate, "TIPSO" refers to triisopropylsilanyloxy, "TBSO" refers to tert-butyl-dimethyl-silanyloxy.

The Examples provided herein are illustrative of the invention claimed herein and are not intended to limit the scope of the claimed invention in any way. The preparations and examples are named using AutoNom 2.2 in ChemDraw Ultra, or AutoNom 2000 in MDL ISIS/Draw version 2.5 SPI from MDL Information Systems, Inc., or are provided by Chemical Abstracts Services.

A Varian INOVA 400 MHz spectrometer is used to obtain $^1$H NMR Specta the in the solvent indicated. An Agilent HP1100 instrument equipped with a Mass Spectrometer (Agilent MSD SL) is used to obtain LCMS. A Waters Xterra C18 (2.1×50 mm, 3.5 micron) is used as stationary phase and a standard method is a gradient of 5-100% acetonitrile/methanol (50:50) with 0.2% ammonium formate over 3.5 minutes then held at 100% B for 0.5 minutes at a column temperature of 50° C. and a flow rate of 1.0 mL/min. Another standard method is a gradient of 5-100% acetonitrile/methanol (50:50) with 0.2% ammonium formate over 7.0 minutes then held at 100% B for 1.0 minutes at a column temperature of 50° C. and a flow rate of 1.0 mL/min. Additional MS analysis via Agilent MSD (loop machine) is standard Flow injection Analysis (FIA), no column is present and flow is 0.5 ml/min of 80% MeOH with 6.5 mM Ammonium Acetate for 30 secs run time.

Scheme A

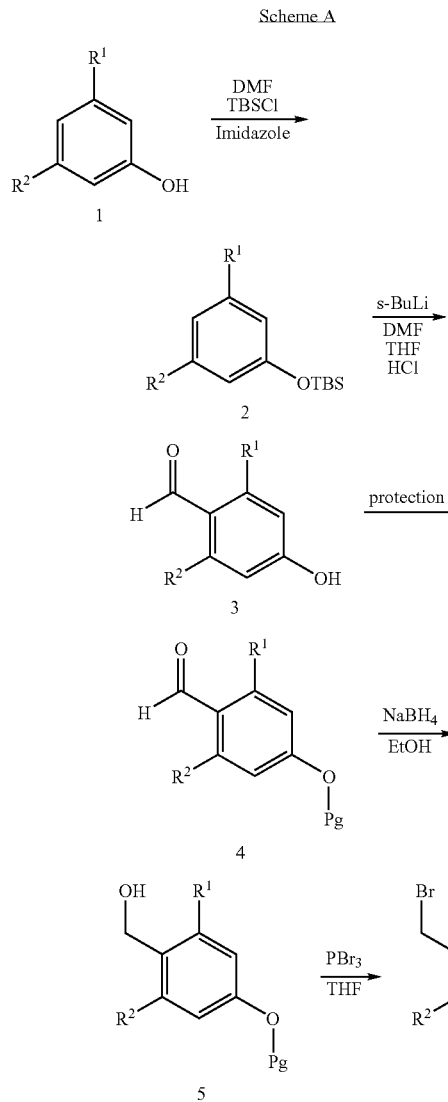

In Scheme A, an optionally substituted phenol (1) is protected (e.g., with TBSCl) to form compound 2, and then compound 2 is converted to the aldehyde (3). Compound 3 is reacted with a compound containing a protecting group (Pg) and leaving group (Lg) to give the ether compound 4. Pg can be —CH$_3$ or —CH$_2$-phenyl and Lg can be mesylate or halo. Preferably, the Lg-Pg compound is I—CH$_3$ or Br—CH$_2$-phenyl. The aldehyde is reduced to form the alcohol (5) and then converted to compound 6. Preferably, compound 5 is halogenated with PBr$_3$ to give the 2-bromo-methyl compound.

Protection and deprotection of the compounds to form compounds of formula I and others are well known to the skilled artisan and are described in the literature. (For example, see: Greene and Wuts, *Protective Groups in Organic Synthesis*, Third Edition, John Wiley and Sons Inc., 1999).

Scheme B

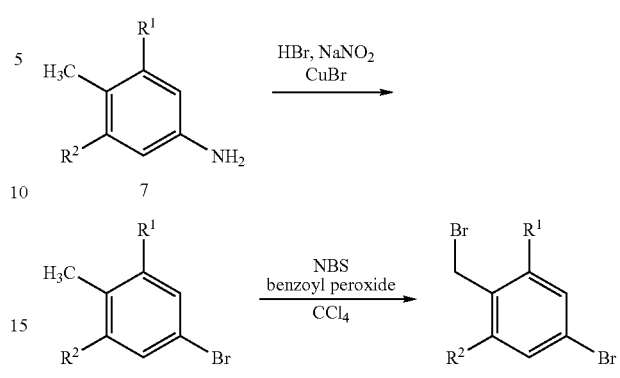

In Scheme B, the aniline (7) is converted the bromo-phenyl (8) which is converted to the bromomethyl compound 9.

Scheme C

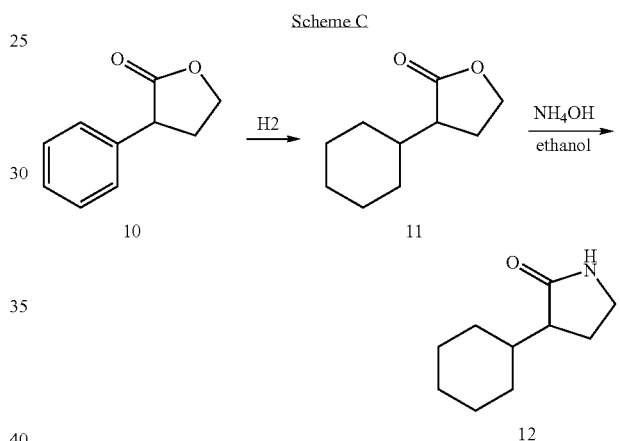

In Scheme C, compound 10 can be synthesized following procedures in the references: *J. Org. Chem.* vol 43, pg 4662 (1978), *Synth Commun* vol 28(18), pg 3305-3315 (1998), and *Synth Commun* vol 28(18), pg 3305-3315 (1998). Compound 10 is reduced to form the cyclohexyl furan-2-one (11) and then to the cyclohexyl pyrrolidin-2-one (12).

Scheme D

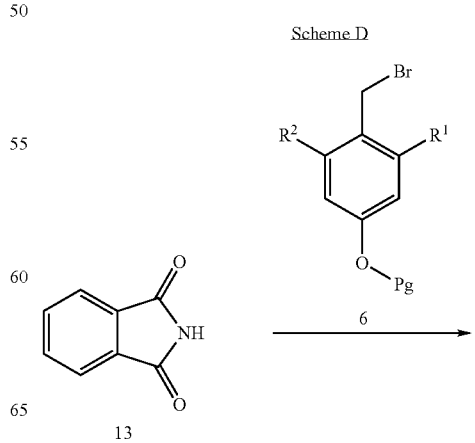

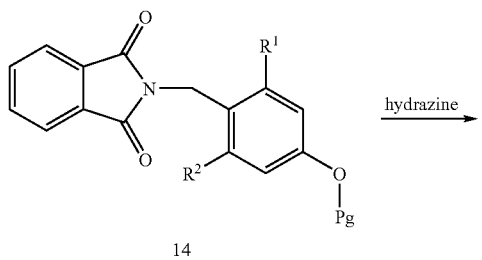
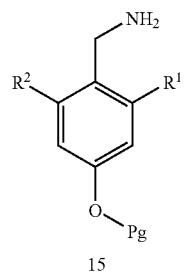
In Scheme D, an appropriately protected benzyl halide (6) is converted to the corresponding benzyl amine in two steps by reaction reacted with potassium thalidomide in a solvent such as DMF and the amine is liberated upon treatment with hydrazine in a solvent such as ethanol.
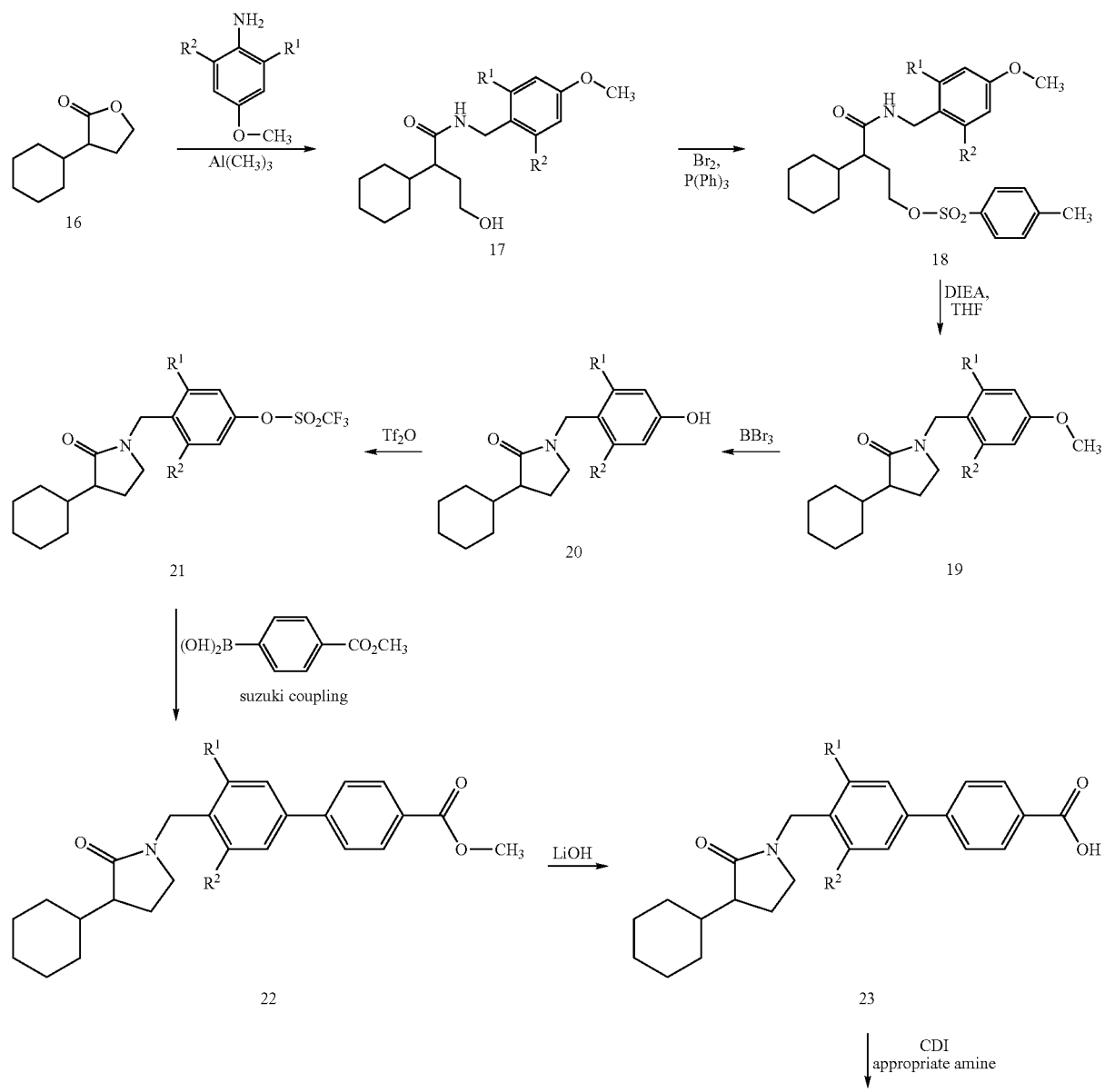

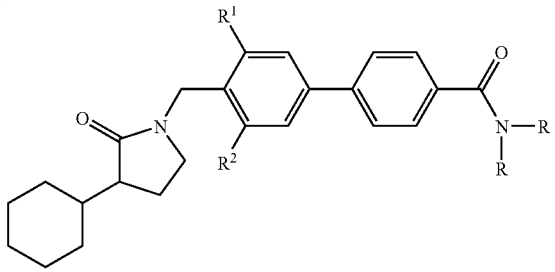

24

In Scheme E, lactone (16) is reacted with a suitably substituted benzyl amine in the presence of trimethylaluminum to afford amide (17) that is converted to the corresponding bromide (18) upon treatment with bromine/triphenylphosphine and a base such as imidazole in a solvent such as dichloromethane. Lactam (19) is formed by treatment of bromide (18) with a base such as diisopropylethylamine in a solvent such as THF with heating. Phenol (20) is formed upon treatment of (19) with boron tribromide and the triflate (21) is formed upon treatment with trifluoromethanesulfonic anhydride and a base such as pyridine. A coupling reaction is performed on (21) using a phenylboronic acid reagent and a catalyst, such as palladium tetrakistriphenylphosphine to prepare an ester that is hydrolyzed to afford acid (23). Acid (23) is coupled with an amine using standard amide coupling conditions such as 1,1'-carbonyldiimidazole to afford amide (24).

Scheme F

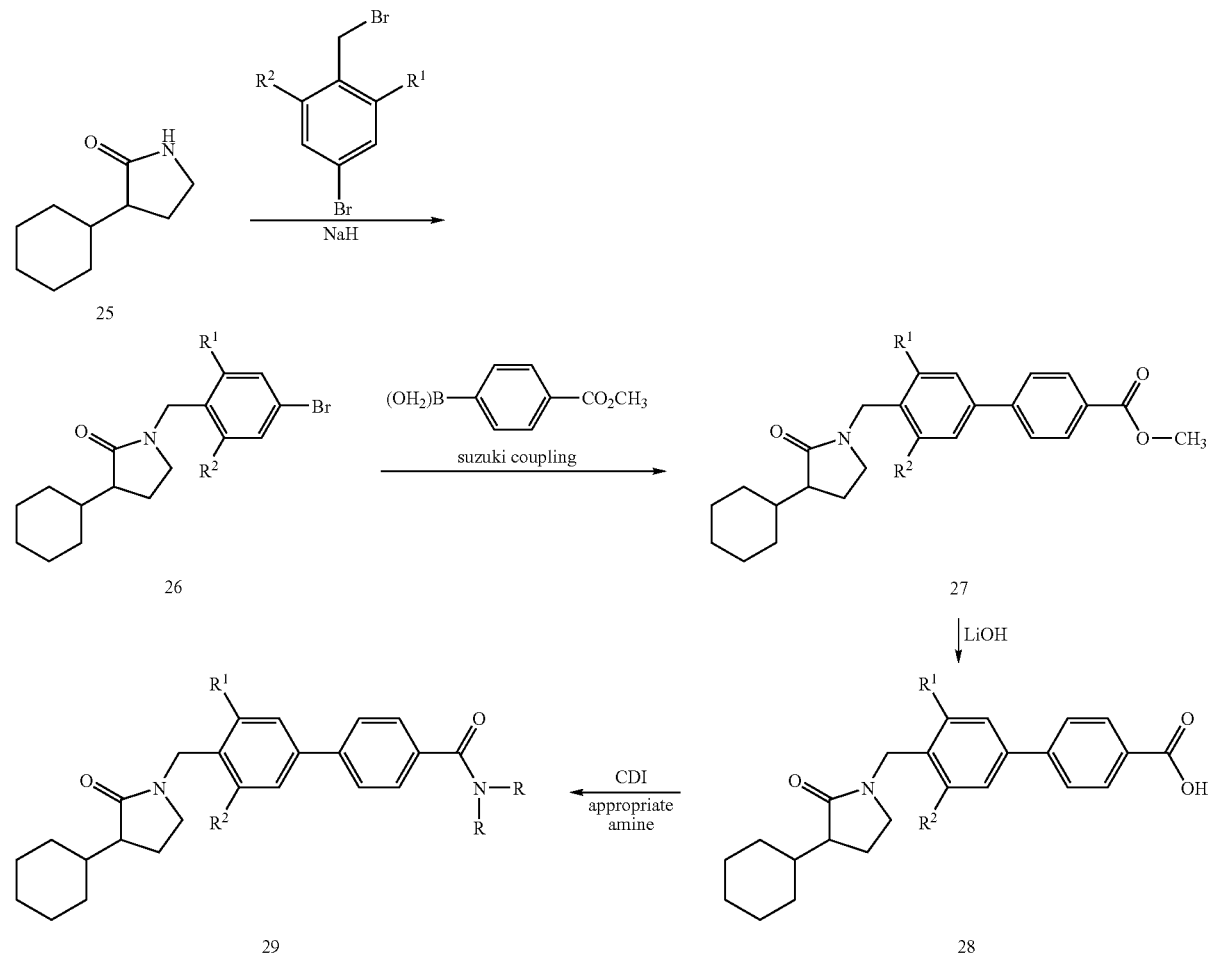

In Scheme F, lactam (25) is alkylated with an appropriately substituted benzyl halide by treatment with a base such as sodium hydride in a solvent such as DMF to prepare bromide (26). A coupling reaction is performed on (26) using a phenylboronic acid reagent and a catalyst, such as palladium tetrakistriphenylphosphine to prepare an ester that is hydrolyzed to afford acid (28). Acid (28) is coupled with an amine using standard amide coupling conditions such as 1,1'-carbonyldiimidazole to afford amide (29).
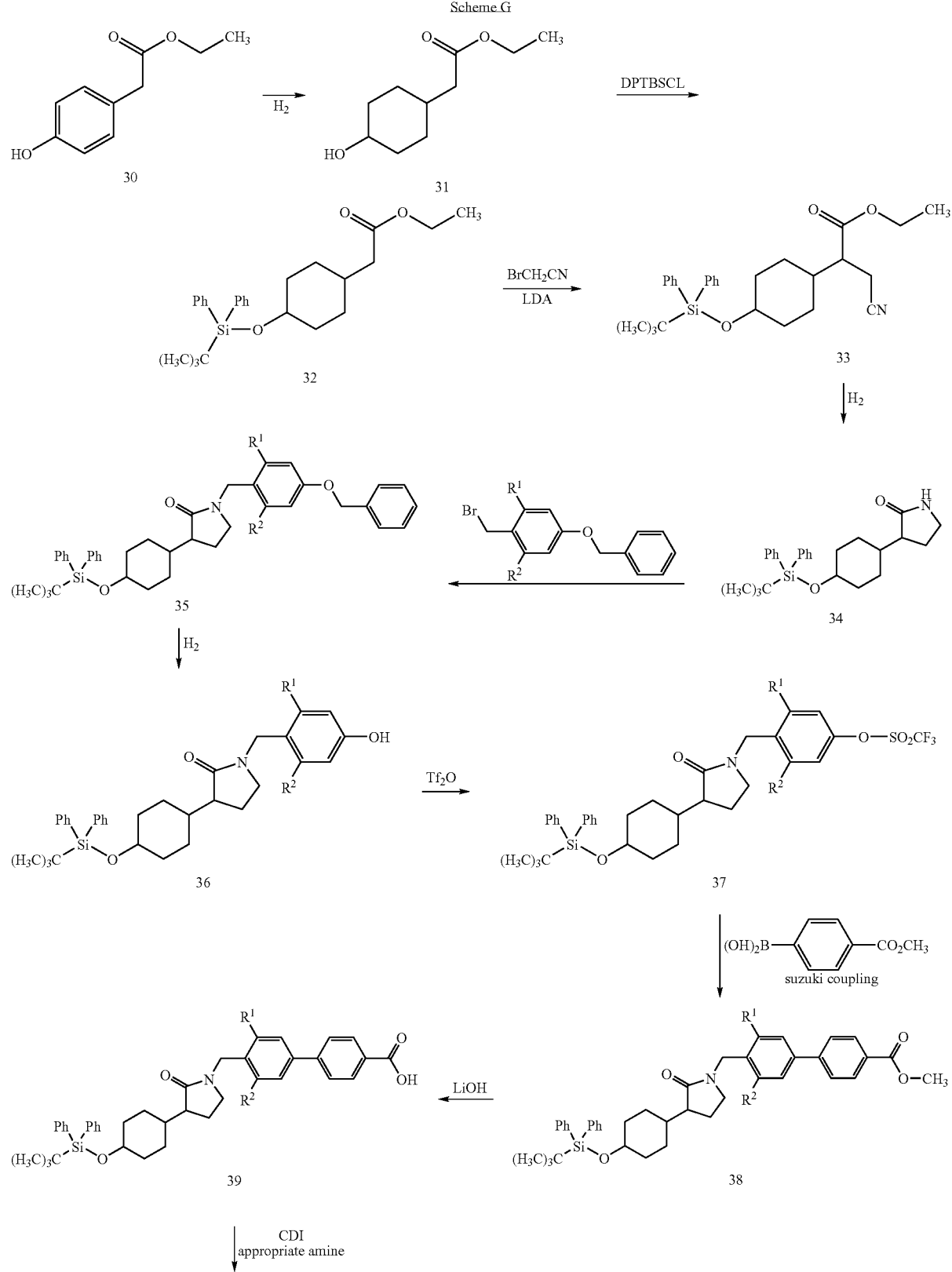
Scheme G

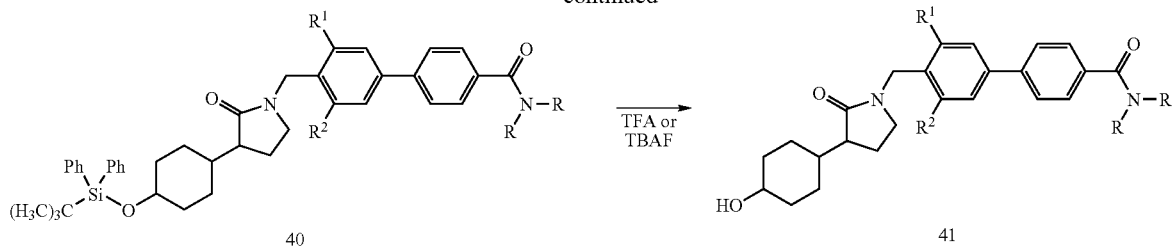

In Scheme G, the phenol (30) is reduced to the corresponding cyclohexyl alcohol (31) by treatment with hydrogen and an appropriate catalyst such as rhodium on aluminum oxide and solvent such as ethanol. The alcohol is protected to form the corresponding tert-butyl diphenyl silyl ether (32) under standard conditions and then is alkylated with bromoacetonitrile using a base such as lithium diisopropyl amide and a solvent such as THF. Nitrile (33) is treated with hydrogen and a suitable catalyst such as $PtO_2$ hydrate and heat to form cyclized lactam (34). Lactam (34) is alkylated with an appropriately substituted benzyl halide by treatment with a base such as sodium hydride in a solvent such as DMF to prepare (35). Phenol (36) is formed upon treatment of (35) with hydrogen and an appropriate catalyst such as 20% $Pd(OH)_2$ on carbon and the triflate (37) is formed upon treatment with trifluoromethanesulfonic anhydride and a base such as pyridine. A coupling reaction is performed on (37) using a phenylboronic acid reagent and a catalyst, such as palladium tetrakistriphenylphosphine to prepare an ester that is hydrolyzed to afford acid (39). Acid (39) is coupled with an amine using standard amide coupling conditions such as 1,1'-carbonyldiimidazole to afford amide (40). The silyl protecting group is removed to afford alcohol (41) under standard conditions such as treatment with TFA.

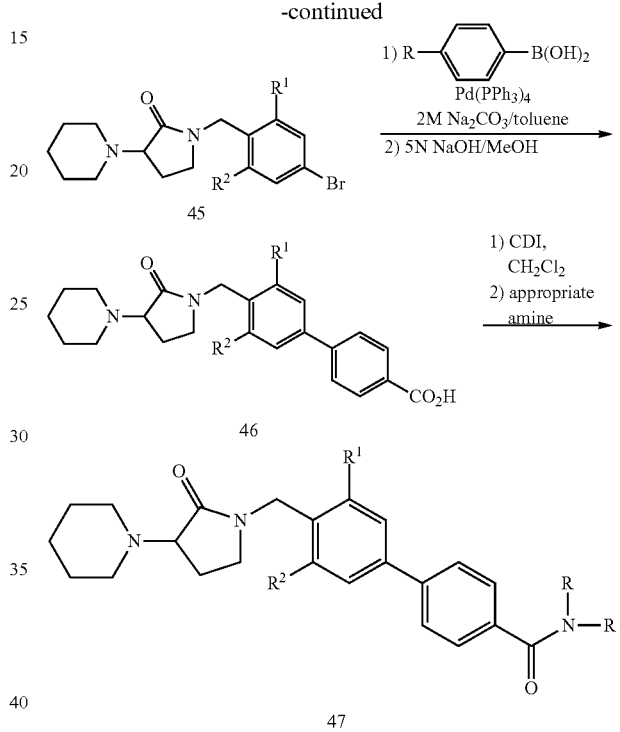

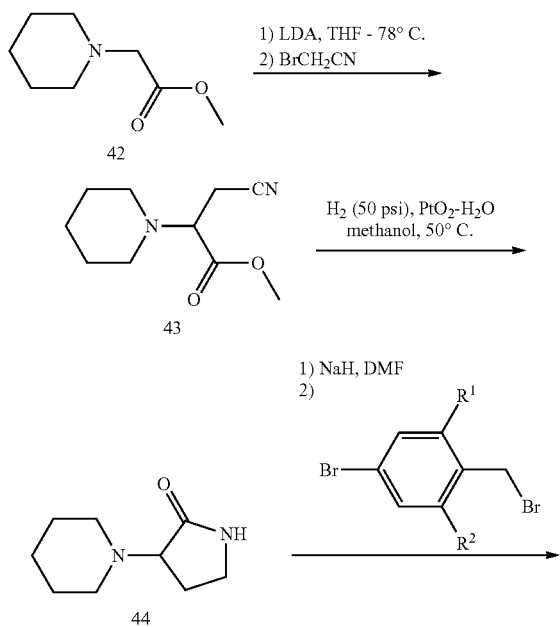

In Scheme H, commercially available ethyl 1-piperidineacetate (42) is reacted with a base such as LDA and is alkylated in a non-protic solvent (preferably THF) with bromoacetonitrile to form compound (43). Nitrile (43) is reduced and cyclized to afford (44) upon treatment with hydrogen and platinum oxide-hydrate in methanol at 50° C. Compound (44) is treated with a base (preferably NaH) and is alkylated with (9) to form (45). A coupling reaction is performed on (45) using a phenylboronic acid reagent and a catalyst, such as palladium tetrakistriphenylphosphine to prepare an ester that is hydrolyzed to afford acid (46). Acid (46) is coupled with an amine using standard amide coupling conditions such as 1,1'-carbonyldiimidazole to afford amide (47).

PREPARATION 1

2,6-dichloro-4-hydroxy-benzaldehyde

Dissolve 3,5 dichlorophenol (1 kg, 6.13 mol) in 3 L dimethylformamide (DMF) and cool to 0° C. Add imidazole (918.74 g, 6.75 mol), followed by tertbutyldimethylsilyl chloride (1017.13 g, 6.75 mol). Warm the mixture to room temperature and stir for 15 minutes. Pour into water (6 L) and extract with ether (4 L). Wash the organic layer with water 2 times, 10% aqueous lithium chloride solution then brine before drying over sodium sulfate. Filter and concentrate under vacuum to obtain tert-butyl-(3,5-dichloro-phenoxy)-dimethyl-silane (1700 g) as an oil.

Dissolve tert-butyl-(3,5-dichloro-phenoxy)-dimethyl-silane (425 g, 1.5 mol) in 4 L dry tetrahydrofuran and cool to −68° C. Slowly add 1.1 equivalents of sec-butyl lithium (103.1 g, 1.61 mol) at −68° C. (~1.75 hr). After addition is complete stir the reaction at −70° C. for 30 min. Add dimethylformamide (168.5 g, 2.3 mol) and stir the reaction at −70° C. for 1 hr. Add 1 M hydrochloric acid in water (3.5 L) and allow the reaction to warm to room temperature.

Pour the reaction mixture into ether (5 L), wash with water then brine. Dry over sodium sulfate and concentrate under vacuum to an orange solid. Triturate with cold dichloromethane and filter to recover 250 g (80%) pale yellow solid.

PREPARATION 2

2,6-dichloro-4-methoxy-benzaldehyde

Combine 2,6-dichloro-4-hydroxy-benzaldehyde (120 g, 628.24 mmol) and potassium carbonate (173.65 g, 1256.5 mmol) in 900 mL dimethylformamide and treat with iodomethane (107 g, 753.9 mmol). Stir the reaction at room temperature for 3 hours. Filter off solids and pour into 6 L of water. Filter solids, wash several times with water, air dry and dissolve in ethyl acetate. Wash with water, followed by brine and then dry over sodium sulfate. Filter and concentrate under vacuum to ~100 mL volume, at which point, solids start to crash out. Filter then concentrate down the filtrate to yield a second crop. Wash with hexane, combine all solids and vacuum dry to yield 112.3 g of off-white, solid: $^1$H NMR (400 MHz, CDCl$_3$) δ 10.41 (s, 1H), 6.90 (s, 2H), 3.87 (s, 3H).

PREPARATION 3

2,6-dichloro-4-benzyloxy-benzaldehyde

Treat a mixture of 2,6-dichloro-4-hydroxy-benzaldehyde (250 g, 1.3 mol) and potassium carbonate (361.8 g, 2.62 mol) in 2 L dimethylformamide with benzyl bromide (268.64 g, 1.57 mol). Stir the reaction at room temperature for 1 hour. Filter off solids and pour into 12 L of water. Filter off solid, wash several times with water, air dry and dissolve in ethyl acetate. Dry over magnesium sulfate, filter and concentrate under vacuum to ~1.5 L. Allow to sit overnight then filter. Wash solid with minimal amount of hexane and vacuum dry. Concentrate the filtrate under vacuum and triturate with hexane to yield a second crop of product which when combined with the first crop equals 245 g white crystals. Repeat to obtain a 3rd crop of 80 g as a light-tan powder (88% overall yield): 1H NMR (400 MHz, DMSO-d6) δ 10.26 (s, 1H), 7.43 (m, 5H), 7.28 (s, 2H), 5.25 (s, 2H).

PREPARATION 4

(2,6-dichloro-4-methoxy-phenyl)-methanol

Suspend 2,6-dichloro-4-methoxy-benzaldehyde (112 g, 546 mmol) in 1500 mL ethanol and cool in an ice bath to 7° C. Add sodium borohydride (20.67, 546 mmol) portionwise to obtain a solution. Remove the ice bath and stir for 2 hours. Carefully add reaction mixture to saturated ammonium chloride solution (~4 L) and stir until fully quenched. Extract with dichloromethane (3×1 L) and dry the combined organic extracts over sodium sulfate. Filter and concentrate under vacuum to yield 113 g of a light-tan solid: 1H NMR (400 MHz, CDCl$_3$) δ 6.86 (s, 2H), 4.86 (s, 2H), 3.78 (s, 3H), 2.07 (s, 1H).

PREPARATION 5

(2,6-dichloro-4-benzyloxy-phenyl)-methanol

Prepare the title compound essentially as prepared by the method of Preparation 4. NMR (DMSO-d$_6$) δ 7.38 (m, 4H), 7.33 (m, 1H), 7.12 (s, 2H), 5.14 (s, 2H), 5.05 (t, 1H), 4.59 (d, 2H).

PREPARATION 6

2-bromomethyl-1,3-dichloro-5-methoxy-benzene

Dissolve (2,6-dichloro-4-methoxy-phenyl)-methanol (113 g, 545.76 mmol) in 1200 mL dry THF and cool to 0 deg under nitrogen. Add PBr$_3$ (59.1 g, 218.3 mmol) under nitrogen and stir at 0° C. for 30 minutes. Pour into saturated aqueous NaHCO$_3$ and extract with EtOAc. Dry and concentrate under vacuum to obtain 129.4 g product as an off-white solid. NMR (CDCl$_3$) δ 6.88 (s, 2H), 4.73 (s, 2H), 3.79 (s, 3H).

PREPARATION 7

2-bromomethyl-1,3-dichloro-5-benzyloxy-benzene

Prepare the title compound essentially as prepared by the method of Preparation 6 in an 89% yield. ES MS (m/z): 347 (M+1).

PREPARATION 8

3,5-dichloro-4-methylaniline

Dissolve 1,3-dichloro-2-methyl-5-nitrobenzene (0.50 g, 2.43 mmol) in DMF and treat with tin (II) chloride dihydrate (2.74 g, 12.1 mmol) in a single portion. Stir the reaction for 1 hour, dilute with ethyl acetate, and filter through celite. Wash the filtrate four times with water and twice with brine, dry over MgSO$_4$, filter and concentrate to a dark oil. Purify the residue by silica gel chromatography eluting with a gradient of 5% to 10% ethyl acetate in hexanes to give 342 mg (80%) of the titled product as white flakes.

PREPARATION 9

5-bromo-1,3-dichloro-2-methylbenzene

Suspend 3,5-dichloro-4-methylaniline in 48% HBr (5 mL) and water (5 mL) and heat with a heat gun until the mixture is near the boiling point. Cool the slurry to room temperature and then cool to 0° C. with an ice/brine bath. Add dropwise a solution of sodium nitrite (109 mg, 1.58 mmol) in water (2 mL). After the addition is complete, stir the reaction an additional 15 min in the cold bath. Add a solution of CuBr (1.08 g, 7.53 mmol) in 48% HBr (2 mL) and heat the rapidly stirring reaction to 50° C. for 1 hour. Cool the reaction to room temperature, dilute with EtOAc and discard the aqueous layer. Wash the organic layer with water and brine, dry with MgSO$_4$, filter through celite and concentrate to an orange residue. Purify the residue by silica gel chromatography eluting with hexanes to afford 164 mg (45%) of the product as a yellow solid.

PREPARATION 10

5-bromo-2-(bromomethyl)-1,3-dichlorobenzene

Heat to reflux a solution of 5-bromo-1,3-dichloro-2-methylbenzene (97 mg, 0.40 mmol), N-bromosuccinimide (76 mg, 0.425 mmol) and benzoyl peroxide (16 mg, 0.06 mmol) in $CCl_4$ (5 mL) for 3 hours under $N_2$. Cool the reaction to room temperature and concentrate to an orange residue. Purify the residue by silica gel chromatography eluting with hexanes to afford 112 mg (87%) of the product as white crystals.

PREPARATION 11

3-Cyano-3-phenyl-propionic acid ethyl ester

Prepare the title compound by the procedure described in *J. Org. Chem* vol 43, pg 4662 (1978).

PREPARATION 12

4-Hydroxy-2-phenyl-butyronitrile

Prepare the title compound by the procedure described in *Synth Commun* vol 28(18), pg 3305-3315 (1998).

PREPARATION 13

3-Phenyl-dihydro-furan-2-one

Prepare the title compound by the procedure described in *Synth Commun* vol 28(18), pg 3305-3315 (1998).

PREPARATION 14

3-Cyclohexyl-dihydro-furan-2-one

Stir a mixture of 3-phenyl-dihydro-furan-2-one (9.0 g), rhodium on carbone (5%, 3.62 g) and ethanol (220 mL) on a hydrogenation parr shaker at 60 psi, 60° C. for 18 hours. Remove the reaction from the parr shaker and filter the mixture through celite, concentrate the filtrate to afford 8.6 g (92%) of the title compound.

PREPARATION 15

3-Cyclohexyl-pyrrolidin-2-one

Heat a mixture of 3-cyclohexyl-dihydro-furan-2-one (32.2 g), ammonium hydroxide (700 mL) and ethanol (700 mL) at 230° C. in a sealed steel bottle for 18 hours. Cool the reaction and remove the solvent in vacuo. Partition the residue with ethyl acetate (500 mL) and HCl (1N, 300 mL). Dry the organic over sodium sulfate. After filtration and concentration, recrystallize with 1:3 ethyl acetate:hexane to afford 30 grams (94%) of the title compound.

PREPARATION 16

2-(2,6-Dichloro-4-methoxy-benzyl)-isoindole-1,3-dione

Stir a mixture of potassium phthalimide (1.85 g, 10 mmol), 2-bromomethyl-1,3-dichloro-5-methoxy-benzene (2.68 g, 10 mmol) and DMF (20 mL) at 50° C. for 12 hours. Cool the reaction and dilute with ethyl acetate (60 mL) and wash with water three times and brine one time. After drying the organic layer over sodium sulfate, filter and concentrate under vacuum. Purify the residue by silica gel chromatography with 1:3 ethyl acetate/hexane to afford 2.74 g (82%) of the title compound. MS (m/z): 336 $(M+H)^+$.

PREPARATION 17

2,6-Dichloro-4-methoxy-benzylamine hydrochloride

Treat a solution of 2-(2,6-Dichloro-4-methoxy-benzyl)-isoindole-1,3-dione (2.74 g, 8.18 mmol) in ethanol with hydrazine hydrate (0.61 g, 12.27 mmol) at 70° C. for 12 hours. Cool the reaction and filter the precipitate. Concentrate the filtrate and partition the residue with ethyl acetate and water. After drying the organic layer over sodium sulfate, filter and concentrate under vacuum. To the residue, add ethyl acetate (20 mL) and HCl (4 N in dioxane, 5 mL). Collect the white crystal by filtration and air dry to afford 1.65 g (84%) of the title compound. MS (m/z): 242 $(M+H)^+$.

PREPARATION 18

2-Cyclohexyl-N-(2,6-dichloro-4-methoxy-benzyl)-4-hydroxy-butyramide

Treat a mixture of 2,6-dichloro-4-methoxy-benzylamine hydrochloride (4.0 g, 16.6 mmol) and toluene (100 mL) with trimethylaluminum (2 M in toluene, 16.6 mL, 33.2 mmol) at room temperature for 10 minutes. To the mixture, add a solution of 3-cyclohexyl-dihydro-furan-2-one (2.51 g, 14.94 mmol) in toluene (50 mL). Stir the reaction at reflux for 6 hours. Cool the reaction and quench with HCl (1 N, 50 mL). Partition the mixture with ethyl acetate and HCl (1 N). Separate the organic layer and wash with water and brine. After drying the organic layer over sodium sulfate and filtration, concentrate the filtrate to afford 4.5 g (81%) of the title compound as white solid. MS (m/z): 374 $(M+H)^+$.

PREPARATION 19

4-Bromo-2-cyclohexyl-N-(2,6-dichloro-4-methoxy-benzyl)-butyramide

Stir a mixture of triphenylphosphine (3.16 g, 12.06 mmol), bromine (1.91 g, 12.06) and methylene chloride (150 mL) at room temperature for 20 minutes. To the mixture, add a solution of imidazole (0.98 g, 14.48 mmol), 2-Cyclohexyl-N-(2,6-dichloro-4-methoxy-benzyl)-4-hydroxy-butyramide (4.5 g, 12.06 mmol) in methylene chloride (100 mL). Stir the reaction at room temperature for 3.5 hours. Wash the reaction with HCl (1 N), water and brine. After drying the organic layer over sodium sulfate, filter and concentrate under vacuum. Purify the residue by silica gel chromatography with 1:3 ethyl acetate/hexane to afford 2.5 g. of the title compound. MS (m/z): 436 $(M+H)^+$.

PREPARATION 20

Trifluoro-methanesulfonic acid 3,5-dichloro-4-(3-cyclohexyl-2-oxo-pyrrolidin-1-ylmethyl)-phenyl ester Treat a 0° C. solution of 3-cyclohexyl-1-(2,6-dichloro-4-hydroxy-benzyl)-pyrrolidin-2-one (1.20 g, 3.52 mmol) and pyridine (2.4 g, 30 mmol) in $CH_2Cl_2$ (25 mL) with trifluoromethanesulfonic anhydride (2.98 g, 10.56 mmol) for 1 hour. Dilute the reaction with $CH_2Cl_2$ and wash with 1N HCl

PREPARATION 21

(4-Hydroxy-cyclohexyl)-acetic acid ethyl ester

Stir a mixture of (4-hydroxy-phenyl)-acetic acid ethyl ester (78.86 g), Rhodium on aluminum oxide (40%, 31.87 g) and ethanol (1 L) on a hydrogenation parr shaker at 60 psi, 60° C. for 18 hours. Remove the reaction from parr shaker. Filter the mixture through celite and concentrate the to afford 81.25 g (99%) of the title compound.

PREPARATION 22

[4-(tert-Butyl-diphenyl-silanyloxy)-cyclohexyl]-acetic acid ethyl ester

Treat a mixture of (4-hydroxy-cyclohexyl)-acetic acid ethyl ester (17.2 g, 100 mmol), imidazole (8.16 g, 120 mmol) and DMF (150 mL) with tetrabutyl diphenyl silyl chloride (32.8 g, 120 mmol) at room temperature for 12 hours. Dilute the reaction with ether and wash with water three times. After drying the organic layer over sodium sulfate, filtrate and concentrate. Purify via flash chromatography using 7% ethyl acetate in hexanes to afford 32.5 g (80%) of the title compound. MS (m/z): 411 (M+).

PREPARATION 23

2-[4-(tert-Butyl-diphenyl-silanyloxy)-cyclohexyl]-3-cyano-propionic acid ethyl ester Treat a −78° C. solution of [4-(tert-butyl-diphenyl-silanyloxy)-cyclohexyl]-acetic acid ethyl ester (4.71 g, 11.49 mmol) in THF (40 mL) with a 1.6M solution of lithium diisopropylamide in THF (7.18 mL, 14.36 mmol) and stir at −78° C. for 20 minutes under $N_2$. Treat the reaction with bromoacetonitrile (1.71 g, 14.36 mol) and stir at −78° C. for 2 hours. Warm the reaction to room temperature and stir for 2 hours. Quench the reaction with 1N HCl at 0° C. Dilute the reaction with ethyl acetate and wash with water. Dry the organic layer ($Na_2SO_4$), remove the solvent in vacuo to afford crude product, and purify with a 25% to 40% ethyl acetate in hexanes gradient to afford 2.62 g (50%) of the titled product. MS (m/z): 450 (M+1).

PREPARATION 24

3-[4-(tert-Butyl-diphenyl-silanyloxy)-cyclohexyl]-pyrrolidin-2-one

Purge a mixture of 2-[4-(tert-butyl-diphenyl-silanyloxy)-cyclohexyl]-3-cyano-propionic acid ethyl ester (2.6 g) and $PtO_2$ hydrate (0.8 g) in ethanol (30 mL) with $N_2$ and then stir under 50 psi of $H_2$ at 50° C. for 16 hours. Cool the reaction and filter through celite. Remove the solvent from the filtrate in vacuo to afford crude product and purify with a 50% ethyl acetate in hexanes to 100% ethyl acetate gradient to afford 0.75 g (31%) of the titled product. MS (m/z): 422 (M+).

PREPARATION 25

1-(4-Benzyloxy-2,6-dichloro-benzyl)-3-[4-(tert-butyl-diphenyl-silanyloxy)-cyclohexyl]-pyrrolidin-2-one Treat a solution of 3-[4-(tert-butyl-diphenyl-silanyloxy)-cyclohexyl]-pyrrolidin-2-one (0.75 g, 1.78 mmol) in DMF (25 mL) with 60% sodium hydride (0.11 g, 2.67 mmol) and stir at room temperature for 15 minutes under $N_2$. Cool the reaction to 0° C., treat with 2-bromomethyl-1,3-dichloro-5-benzyloxy-benzene (0.74 g, 2.13 mmol), and stir for 30 minutes at 0° C. Warm to room temperature and stir for 30 minutes under $N_2$. Quench the reaction with water and dilute with diethyl ether. Wash the organic layer with water three times, dry ($Na_2SO_4$), and remove the solvent in vacuo to afford crude product. Purify with a 0 to 30% ethyl acetate in hexanes gradient to afford 1.2 g (99%) of the titled product. MS (m/z): 686 (M+).

PREPARATION 26

3-[4-(tert-Butyl-diphenyl-silanyloxy)-cyclohexyl]-1-(2,6-dichloro-4-hydroxy-benzyl)-pyrrolidin-2-one Purge a mixture of 3-(4-benzyloxy-2,6-dichloro-benzyl)-3-[4-(tert-butyl-diphenyl-silanyloxy)-cyclohexyl]-pyrrolidin-2-one (1.15 g) and 20% palladium (II) hydroxide on carbon (0.200 g) in ethanol (25 mL) with $N_2$ and $H_2$ and stir under a balloon of $H_2$ for 12 hours at room temperature. Filter the mixture through celite. Concentrate the filtrate in vacuo to afford 0.62 g (62%) of the titled product. MS (m/z): 596 (M+).

PREPARATION 27

Trifluoro-methanesulfonic acid 4-{3-[4-(tert-butyl-diphenyl-silanyloxy)-cyclohexyl]-2-oxo-pyrrolidin-1-ylmethyl}-3,5-dichloro-phenyl ester Treat a mixture of 3-[4-(tert-Butyl-diphenyl-silanyloxy)-cyclohexyl]-1-(2,6-dichloro-4-hydroxy-benzyl)-pyrrolidin-2-one (0.62 g, 1.04 mmol), pyridine (0.41 g, 5.21) and dichloromethane (15 mL) at 0° C. with trifluoromethanesulfonic anhydride (0.59 g, 2.08 mmol). Stir the reaction for 1 hour at 0° C. and 1 hour at room temperature. Remove excess pyridine in vacuo, and to the residue, add dichloromethane and wash with water and saturated ammonium chloride. Dry the organic layer ($Na_2SO_4$), remove the solvent in vacuo, and purify the crude product on silica gel column with 20% ethyl acetate in to afford 0.61 g (80%) of the title compound. MS (m/z): 728 (M+).

PREPARATION 28

4'-{3-[4-(tert-Butyl-diphenyl-silanyloxy)-cyclohexyl]-2-oxo-pyrrolidin-1-ylmethyl}-3',5'-dichloro-biphenyl-4-carboxylic acid methyl ester Bring a mixture of trifluoro-methanesulfonic acid 4-{3-[4-(tert-butyl-diphenyl-silanyloxy)-cyclohexyl]-2-oxo-pyrrolidin-1-ylmethyl}-3,5-dichloro-phenyl ester (0.61 g, 0.84 mmol), 4-methoxycarbonylphenylboronic acid (0.18 g, 1 mmol), sodium carbonate (0.267 g, 2.52 mmol) in THF (15 mL) and water (5 mL) to 60° C. To the mixture at 60° C., add Pd(PPh$_3$)$_4$ (0.048 g, 0.04 mmol). Raise the reaction temperature to 80° C. and stir for 1 hour. Cool the reaction, dilute with ethyl acetate, and wash with water and brine. Dry the organic layer ($Na_2SO_4$), remove the solvent in vacuo to afford crude product, and purify on silica gel column with 25% ethyl acetate in hexanes to afford 0.56 g (93%) of the titled product. MS (m/z): 714 (M+).

PREPARATION 29

4'-{3-[4-(tert-Butyl-diphenyl-silanyloxy)-cyclohexyl]-2-oxo-pyrrolidin-1-ylmethyl}-3',5'-dichloro-biphenyl-4-carboxylic acid Treat a solution of 4'-{3-[4-(tert-butyl-diphenyl-silanyloxy)-cyclohexyl]-2-oxo-pyrrolidin-1-ylmethyl}-3',5'-dichloro-biphenyl-4-carboxylic acid methyl ester (0.56 g) in THF (5 mL) and methanol (1 mL) with 2N LiOH (5 mL) and stir at 50° C. for 2 hours. Cool the reaction, dilute with ethyl acetate (25 mL), and wash with 1 N HCl (10 mL). Dry the organic layer ($Na_2SO_4$) and remove the solvent in vacuo to afford 0.55 g (99%) of the title compound. MS (m/z): 700 (M+).

PREPARATION 30

3-[4-(tert-Butyl-diphenyl-silanyloxy)-cyclohexyl]-1-[3,5-dichloro-4'-(4-trifluoromethyl-piperidine-1-carbonyl)-biphenyl-4-ylmethyl]-pyrrolidin-2-one Treat a solution of 4'-{3-[4-(tert-Butyl-diphenyl-silanyloxy)-cyclohexyl]-2-oxo-pyrrolidin-1-ylmethyl}-3',5'-dichloro-biphenyl-4-carboxylic acid (0.35 g, 0.5 mmol) in $CH_2Cl_2$ (20 mL) with 1,1'-carbonyldiimidazole (0.162 g, 1.0 mmol) and stir for 45 minutes at room temperature. Treat the reaction with 4-trifluoromethylpiperidine hydrochloride (0.142 g, 0.75 mmol) and diisopropylethylamine (0.097 g, 0.75 mmol), and stir for 12 hours at room temperature. Load the mixture on silica gel column and flash with 25% to 50% ethyl acetate in hexanes to afford 0.21 g (50%) of the title compound. MS (m/z): 835 (M+).

PREPARATION 31

3-Cyano-2-piperidin-1-yl-propionic acid ethyl ester

Treat a −78° C. solution of ethyl 1-piperidine acetate (20.0 g, 0.117 mol) in THF (200 mL) with a 2M solution of lithium diisopropylamide in heptane/THF/ethylbenzene (70.1 mL, 0.140 mol) and stir at −78° C. for 20 minutes under $N_2$. Treat the reaction with bromoacetonitrile (21.00 g, 0.175 mol) and stir at −78° C. for 15 minutes. Warm the reaction to room temperature and stir 4 hours. Quench the reaction into saturated ammonium chloride. Dilute the reaction with ethyl acetate and wash with water. Dry the organic layer ($Na_2SO_4$), remove the solvent in vacuo to afford crude product, and purify with a 0 to 20% ethyl acetate in hexanes gradient to afford 6.74 g (27%) of the titled product. $R_f$=0.41 (3/1 hexanes/ethyl acetate). ES MS (m/z): 211 (M+1).

PREPARATION 32

3-Piperidin-1-yl-pyrrolidin-2-one

Purge a mixture of 3-cyano-2-piperidin-1-yl-propionic acid ethyl ester (2.36 g, 11.2 mmol) and $PtO_2$ hydrate (0.400 g) in methanol (40 mL) with $N_2$ and stir under 50 psi of $H_2$ at 50° C. for 16 hours. Cool the reaction and filter through hyflo. Remove the solvent from the filtrate in vacuo to afford crude product and purify with a 0 to 10% methanol in $CH_2Cl_2$ gradient to afford 1.11 g (59%) of the titled product. $R_f$=0.18 (9/1 $CH_2Cl_2$/methanol). ES MS (m/z): 169 (M+).

PREPARATION 33

(4,4-Difluoro-piperidin-1-yl)-acetic acid methyl ester

Treat a ° C. solution of 4,4-difluoropiperidin HCl (17.91 g, 0.113 mol) and $(CH_3CH_2)_3N$ (28.75 g, 0.284 mol) in $CH_2Cl_2$ (250 mL) with methyl bromoacetate (17.37 g, 0.113 mol), warm to room temperature, and stir 16 hours at room temperature under $N_2$. Dilute the reaction with saturated $NaHCO_3$ and water and extract twice with 3:1 chloroform:isopropanol. Dry the organic layer ($Na_2SO_4$), remove the solvent in vacuo to afford crude product, and purify with 0 to 5% methanol in $CH_2Cl_2$ to afford 14.22 g (65%) of the titled product. $R_f$=0.77 (9/1 $CH_2Cl_2$/methanol). ES MS (m/z): 194 (M+).

PREPARATION 34

(4-Hydroxy-piperidin-1-yl)-acetic acid methyl ester

Treat a 0° C. solution of 4-hydroxy-piperidine (20.0 g, 0.19 mol) and $(CH_3CH_2)_3N$ (24.0 g, 0.24 mol) in $CH_2Cl_2$ (200 mL) with methyl bromoacetate (30.21 g, 0.197 mol), warm to room temperature, and stir 2 hours at room temperature under $N_2$. Dilute the reaction with water and extract with 3:1 chloroform:isopropanol. Dry the organic layer ($Na_2SO_4$), remove the solvent in vacuo to afford crude product, and purify with a 5% methanol in $CH_2Cl_2$ to afford 20.13 g (59%) of the titled product. $R_f$=0.13 (9/1 $CH_2Cl_2$/methanol). ES MS (m/z): 174 (M+).

PREPARATION 35

[4-(tert-Butyl-diphenyl-silanyloxy)-piperidin-1-yl]-acetic acid methyl ester

Treat a solution of (4-hydroxy-piperidin-1-yl)-acetic acid methyl ester (10.0 g, 57.7 mmol) and imidazole (4.71 g, 69.2 mmol) in DMF (100 mL) with t-butyl-diphenylsilyl chloride (19.04 g, 69.3 mmol) and stir for 16 hours at room temperature. Dilute the reaction with diethyl ether and wash with water. Dry the organic layer ($Na_2SO_4$), remove the solvent in vacuo to afford crude product, and purify with a 2% methanol in $CH_2Cl_2$ to afford 17.38 g (73%) of the titled product. $R_f$=0.71 (9/1 $CH_2Cl_2$/methanol). ES MS (m/z): 412 (M+).

PREPARATION 36

2-[4-(tert-Butyl-diphenyl-silanyloxy)-piperidin-1-yl]-3-cyano-propionic acid methyl ester Treat a −78° C. solution of 4-(tert-butyl-diphenyl-silanyloxy)-piperidin-1-yl]-acetic acid methyl ester (17.36 g, 42.2 mmol) in THF (100 mL) with a 2M solution of lithium diisopropylamide in heptane/THF/ethylbenzene (25.3 mL, 50.6 mmol) and stir at −78° C. for 15 minutes under $N_2$. Warm the reaction to −20° C. and then re-cool to −78° C. Treat the reaction with bromoacetonitrile (7.57 g, 63.2 mmol) and stir at −78° C. for 15 minutes. Warm the reaction to room temperature and stir 2 hours. Acidify the reaction and quench into saturated NH₄Cl. Dilute the reaction with ethyl acetate and wash with water. Dry the organic (Na₂SO₄) and remove the solvent in vacuo to afford crude product, and purify with a 0 to 100% ethyl acetate in hexanes gradient to afford 4.83 g (25%) of the titled product. $R_f$=0.51 (1/1 hexanes/ethyl acetate). ES MS (m/z): 451 (M+).

PREPARATION 37

3-[4-(tert-Butyl-diphenyl-silanyloxy)-piperidin-1-yl]-pyrrolidin-2-one

Treat a 0° C. mixture of 2-[4-(tert-butyl-diphenyl-silanyloxy)-piperidin-1-yl]-3-cyano-propionic acid methyl ester (3.32 g, 7.40 mmol) and cobalt (II) chloride hexahydrate (0.87 g, 3.65 mmol) in THF (60 mL) and water (30 mL) portion-wise with sodium borohydride (1.39 g, 36.7 mmol), warm to room temperature, and stir for 2 days under N₂. Treat the reaction with 28% ammonium hydroxide (1 mL) and filter through hyflo. Remove the solvent from the filtrate in vacuo, dilute the residue with minimal water and brine, and extract three times with 3:1 chloroform:isopropanol. Dry the organic layer (Na₂SO₄), remove the solvent in vacuo to afford crude product, and purify with a 0 to 10% methanol in CH₂Cl₂ gradient to afford 1.68 g (54%) of the titled product. $R_f$=0.39 (9/1 CH₂Cl₂/methanol). ES MS (m/z): 423 (M+).

PREPARATION 38

1-(4-Benzyloxy-2,6-dichloro-benzyl)-3-[4-(tert-butyl-diphenyl-silanyloxy)-piperidin-1-yl]-pyrrolidin-2-one Treat a −78° C. solution of 3-[4-(tert-butyl-diphenyl-silanyloxy)-piperidin-1-yl]-pyrrolidin-2-one (0.25 g, 0.59 mmol) in THF (6 mL) with a 1.6 M n-butyl lithium in hexanes (0.37 mL, 0.59 mmol) and stir at −78° C. for 10 minutes under N₂. Treat the reaction with 5-benzyloxy-2-bromomethyl-1,3-dichloro-benzene (0.204 g, 0.59 mmol), warm to room temperature, and stir for 16 hours under N₂. Re-cool the reaction to −78° C., treat with 1.6 M n-butyl lithium in hexanes (0.37 mL, 0.59 mmol), warm to room temperature, and stir for 2 hours. Quench the reaction with water and extract with ethyl acetate. Dry the organic layer (Na₂SO₄), remove the solvent in vacuo to afford crude product, and purify with a 50 to 100% ethyl acetate in hexanes gradient to afford 0.263 g (65%) of the titled product. $R_f$=0.18 (3/1 ethyl acetate/hexanes). ES MS (m/z): 687 (M+).

PREPARATION 39

8-(tert-Butyl-diphenyl-silanyloxy)-2-(2,6-dichloro-4-hydroxy-benzyl)-2-aza-spiro[4.5]decan-1-one Purge a mixture of 1-(4-benzyloxy-2,6-dichloro-benzyl)-3-[4-(tert-butyl-diphenyl-silanyloxy)-piperidin-1-yl]-pyrrolidin-2-one (0.452 g, 0.65 mmol) and 20% palladium (II) hydroxide on carbon (90 mg) in THF (10 mL) and ethyl acetate (10 mL) with N₂ and H₂ and stir under a balloon of H₂ for 16 hours at room temperature. Add sodium sulfate to the mixture and filter through hyflo. Remove the solvent in vacuo from the filtrate to afford 0.354 g (90%) of the titled product. $R_f$=0.45 (9/1 CH₂Cl₂/methanol). ES MS (m/z): 597 (M+).

PREPARATION 40

Trifluoro-methanesulfonic acid 4-{3-[4-(tert-butyl-diphenyl-silanyloxy)-piperidin-1-yl]-2-oxo-pyrrolidin-1-ylmethyl}-3,5-dichloro-phenyl ester Treat a 0° C. solution of 8-(tert-butyl-diphenyl-silanyloxy)-2-(2,6-dichloro-4-hydroxy-benzyl)-2-aza-spiro[4.5]decan-1-one (0.351 g, 0.58 mmol), pyridine (0.140 g, 1.77 mmol) and 4-dimethylaminopyridine (0.007 g, 0.057 mmol) in CH₂Cl₂ (12 mL) with trifluoromethanesulfonic anhydride (0.284 g, 1.01 mmol) and stir for 1 hour at 0° C. under N₂. Dilute the reaction with CH₂Cl₂ and wash with water. Dry the organic layer (Na₂SO₄), remove the solvent in vacuo to afford crude product, and purify with a 0 to 10% methanol in CH₂Cl₂ gradient to afford 0.363 g (85%) of the titled product. $R_f$=0.66 (9/1 CH₂Cl₂/methanol). ES MS (m/z): 729 (M+).

PREPARATION 41

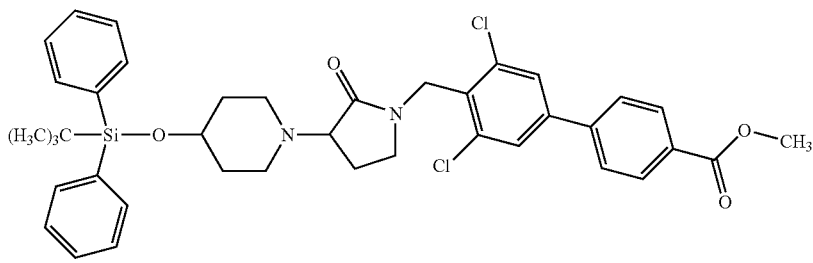

A mixture of trifluoro-methanesulfonic acid 4-{3-[4-(tert-butyl-diphenyl-silanyloxy)-piperidin-1-yl]-2-oxo-pyrrolidin-1-ylmethyl}-3,5-dichloro-phenyl ester (0.357 g, 0.49 mmol) and 4-methoxycarbonyl phenylboronic acid (0.106 g, 0.589 mmol) in THF (8 mL) and 2M sodium carbonate (0.73 mL) is purged with N₂. The reaction is treated with Pd(PPh₃)₄ (0.028 g, 0.024 mmol) and heated to 80° C. for 1 hour under N₂. The reaction is cooled and diluted with ethyl acetate and washed with water. Dry the organic layer (Na₂SO₄), remove the solvent in vacuo to afford crude product, and purify with a 50 to 85% ethyl acetate in hexanes gradient to afford 0.249 g (71%) of the titled product. $R_f$=0.16 (3/1 hexanes/ethyl acetate). MS (m/z): 715 (M+).

PREPARATION 42

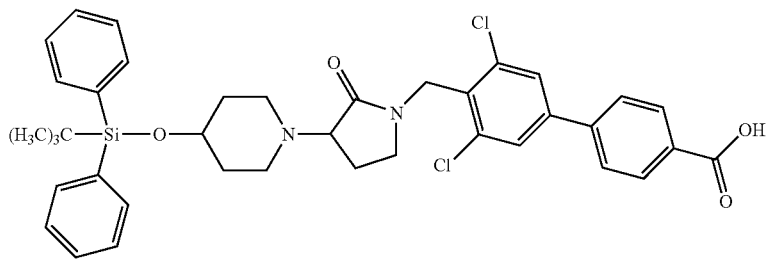

Treat a mixture of Preparation 41 (0.246 g, 0.344 mmol) in THF (15 mL) and methanol (3 mL) with 2M lithium hydroxide (0.86 mL) and stir for 16 hours at room temperature. Neutralize the reaction with 1N HCl and extract with ethyl acetate and water. Dry the organic layer (Na$_2$SO$_4$) and remove the solvent in vacuo to afford 0.245 g (100%) of the titled product. R$_f$=0.38 (9/1 CH$_2$Cl$_2$/methanol). ES MS (m/z): 701 (M+).

PREPARATION 43

3-[4-(tert-Butyl-diphenyl-silanyloxy)-piperidin-1-yl]-1-[3,5-dichloro-4'-(4-trifluoromethyl-piperidine-1-carbonyl)-biphenyl-4-ylmethyl]-pyrrolidin-2-one Treat a solution of Preparation 42 (0.241 g, 0.34 mmol) in CH$_2$Cl$_2$ (10 mL) with 1,1'-carbonyldiimidazole (0.095 g, 0.58 mmol) and stir for 2 hours at room temperature under N$_2$. Treat the reaction with 4-(trifluoromethyl)piperidine HCl (0.130 g, 0.68 mmol) and diisopropylethylamine (0.18 g, 1.38 mmol) and stir for 6 hours at room temperature under N$_2$. Dilute the reaction with ethyl acetate and wash with water. Dry the organic layer (Na$_2$SO$_4$), remove the solvent in vacuo to afford crude product, and purify with a 0 to 10% methanol in CH$_2$Cl$_2$ gradient to afford 0.251 g (87%) of the titled product. R$_f$=0.60 (9/1 CH$_2$Cl$_2$/methanol). ES MS (m/z): 836 (M+).

Scheme I

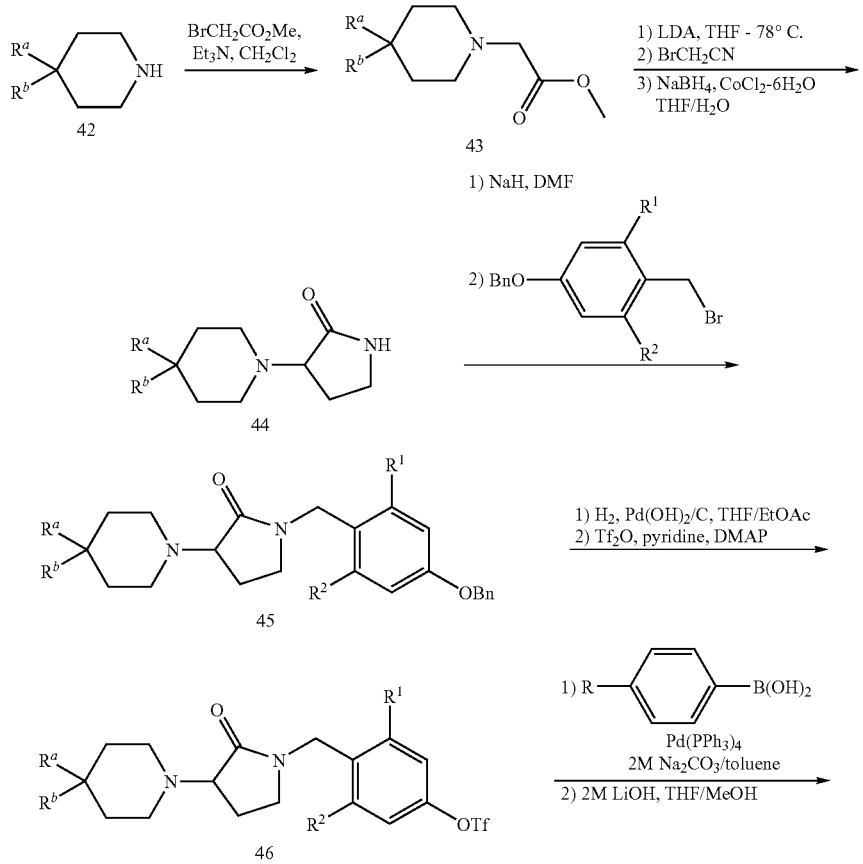

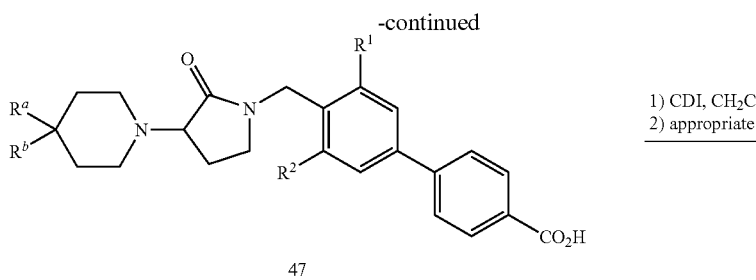

47

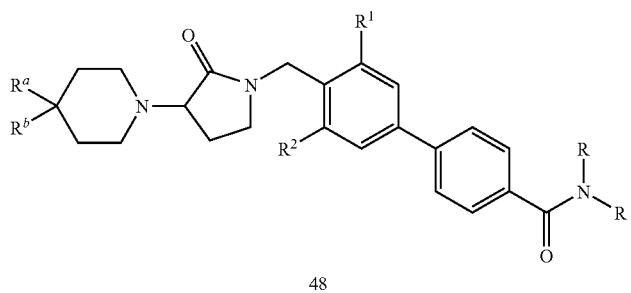

48

In Scheme I, a suitably substituted piperidine is alkylated with bromo ethyl acetate in the presence of a base such as triethyl amine to form ester (43). Ester (43) is reacted with a base such as LDA and is alkylated in a non-protic solvent (preferably THF) with bromoacetonitrile to the nitrile which is reduced and cyclized to afford (44) upon treatment with hydrogen and platinum oxide-hydrate in methanol at 50° C. Compound (44) is treated with a base (preferably NaH) and is alkylated with an appropriately substituted benzyl halide to form (45). Treatment of (45) with hydrogen and an appropriate catalyst such as 20% Pd(OH)$_2$ on carbon affords the corresponding phenol which is treated with trifluoromethanesulfonic anhydride and a base such as pyridine to prepare (46). A coupling reaction is performed on (46) using a phenylboronic acid reagent and a catalyst, such as palladium tetrakistriphenylphosphine to prepare an ester that is hydrolyzed to afford acid (47). Acid (47) is coupled with an amine using standard amide coupling conditions such as 1,1'-carbonyldiimidazole to afford amide (48).

PREPARATION 44

3-Cyano-2-(4,4-difluoro-piperidin-1-yl)-propionic acid methyl ester

Treat a −78° C. solution of (4,4-difluoro-piperidin-1-yl)-acetic acid methyl ester (14.21 g, 73.6 mmol) (Preparation 33) in THF (150 mL) with a 2M solution of lithium diisopropylamide in heptane/THF/ethylbenzene (44.2 mL, 88.4 mmol) and stir at −78° C. for 20 minutes under N$_2$. Treat the reaction with bromoacetonitrile (13.25 g, 110.5 mmol) and stir at −78° C. for 15 minutes. Warm the reaction to room temperature and stir 4 hours. Pour the reaction into saturated NH$_4$Cl. Dilute the reaction with ethyl acetate and wash with water. Dry the organic layer with Na$_2$SO$_4$ and remove the solvent in vacuo to afford crude product. Then, purify on silica with a 0 to 100% ethyl acetate in hexanes gradient to afford 3.74 g (22%) of the titled product. R$_f$=0.50 (1/1 hexanes/ethyl acetate). ES MS (m/z): 233 (M+).

PREPARATION 45

3-(4,4-Difluoro-piperidin-1-yl)-pyrrolidin-2-one

Treat a 0° C. mixture of 3-cyano-2-(4,4-difluoro-piperidin-1-yl)-propionic acid methyl ester (3.74 g, 16.1 mmol) and cobalt (II) chloride hexahydrate (1.92 g, 8.07 mmol) in THF (50 mL) and water (25 mL) portion-wise with sodium borohydride (3.05 g, 80.6 mmol) and warm to room temperature and stir for 2 days under N$_2$. Treat the reaction with 28% ammonium hydroxide (2 mL) and filter through hyflo. Remove the solvent from the filtrate in vacuo and dilute the residue with minimal water and brine and extract three times with 3:1 chloroform:isopropanol. Dry the organic layer with Na$_2$SO$_4$ and remove the solvent in vacuo to afford crude product. Purify on silica with a 0 to 10% methanol in CH$_2$Cl$_2$ gradient to afford 1.53 g (46%) of the titled product. R$_f$=0.43 (9/1 CH$_2$Cl$_2$/methanol, I$_2$ stain). ES MS (m/z): 205 (M+).

PREPARATION 46

1-(2,6-Dichloro-4-hydroxy-benzyl)-3-(4,4-difluoro-piperidin-1-yl)-pyrrolidin-2-one Purge a mixture of 1-(4-benzyloxy-2,6-dichloro-benzyl)-3-(4,4-difluoro-piperidin-1-yl)-pyrrolidin-2-one (3.10 g, 6.62 mmol), 20% palladium (II) hydroxide on carbon (310 mg) in THF (25 mL) and ethyl acetate (100 mL) with N$_2$ and H$_2$ and stir under a balloon of H$_2$ for 6 hours at room temperature. Add sodium sulfate to the mixture and filter through hyflo. Remove the solvent in vacuo from the filtrate to afford 4.41 g of material that is recrystallized from ethyl acetate/CH$_2$Cl$_2$ to afford 1.05 g (42%) of the titled product since there is some de-chlorinated impurities formed during the deprotection. R$_f$=0.48 (9/1 CH$_2$Cl$_2$/methanol). ES MS (m/z): 379 (M+).

PREPARATION 47

Trifluoro-methanesulfonic acid 3,5-dichloro-4-[3-(4,4-difluoro-piperidin-1-yl)-2-oxo-pyrrolidin-1-ylmethyl]-phenyl ester Treat a 0° C. solution of 1-(2,6-dichloro-4-hydroxy-benzyl)-3-(4,4-difluoro-piperidin-1-yl)-pyrrolidin-2-one (1.05 g, 2.78 mmol), pyridine (0.88 g, 11.1 mmol) and 4-dimethylaminopyridine (0.034 g, 0.287 mmol) in CH$_2$Cl$_2$ (20 mL) with trifluoromethanesulfonic anhydride (1.57 g, 5.56 mmol) and stir for 2 hours at 0° C. under N$_2$. Dilute the reaction with CH₂Cl₂ and wash with water. Dry the organic layer with Na₂SO₄ and remove the solvent in vacuo to afford crude product. Purify on silica with 100% ethyl acetate to afford 1.20 g (85%) of the titled product. R_f=0.41 (100% ethyl acetate). ES MS (m/z): 511 (M+).

PREPARATION 48

1-[3,5-Dichloro-4'-(4-carboxylic acid)-biphenyl-4-ylmethyl]-3-(4,4-difluoro-piperidin-1-yl)-pyrrolidin-2-one Treat a mixture of 1-[3,5-dichloro-4'-(4-carboxylic acid methyl ester)-biphenyl-4-ylmethyl]-3-(4,4-difluoro-piperidin-1-yl)-pyrrolidin-2-one (1.03 g, 2.08 mmol) in THF (50 mL) and methanol (5 mL) with 2M lithium hydroxide (5.2 mL) and stir for 16 hours at room temperature. Neutralize the reaction with 1N HCl and extract with ethyl acetate and water. Dry the organic layer with Na₂SO₄ and remove the solvent in vacuo to afford 1.01 g (100%) of the titled product. ES MS (m/z): 483 (M+).

PREPARATION 49

3-(4-methoxyphenyl)-dihydro-furan-2-one

Prepare the title compound by the procedure described in *Synth Commun* [SYNCAV] vol 28(18), pg 3305-3315 (1998).

PREPARATION 50

3-(4-methoxycyclohexyl)-dihydro-furan-2-one

Stir a mixture of 3-(4-methoxyphenyl)-dihydro-furan-2-one (0.98 g), rhodium on carbone (5%, 0.98 g) and ethanol (50 mL) on a hydrogenation parr shaker at 60 psi, 60° C. for 18 hours. Remove the reaction from the parr shaker and filter the mixture through celite, concentrate the filtrate to afford 0.92 g (90%) of the title compound.

PREPARATION 51

3-(4-methoxycyclohexyl)-pyrrolidin-2-one

Heat a mixture of 3-(4-methoxycyclohexyl)-dihydro-furan-2-one (0.91 g), ammonium hydroxide (20 mL) and ethanol (20 mL) at 230° C. in a sealed steel bottle for 12 hours. Cool the reaction and remove the solvent in vacuo. Partition the residue with ethyl acetate (100 mL) and HCl (1N, 60 mL). Dry the organic over sodium sulfate. After filtration and concentration, recrystallize with 1:3 ethyl acetate:hexane to afford 0.71 gram of the title compound.

PREPARATION 52

1-(4-Bromo-2,6-dichloro-benzyl)-3-(4-methoxy-cyclohexyl)-pyrrolidin-2-one

Treat a solution of 3-(4-methoxycyclohexyl)-pyrrolidin-2-one (0.0.71 g, 3.6 mmol) in DMF (20 mL) with a sodium hydride (0.0.29 mL, 7.2 mmol) and stir at room temperature for 10 minutes under N₂. Treat the reaction with 5-Bromo-2-bromomethyl-1,3-dichloro-benzene (1.36 g, 4.3 mmol). Stir the mixture for 14 hours. Quench the reaction with water and extract with ethyl acetate. Dry the organic layer (Na₂SO₄), remove the solvent in vacuo to afford crude product, and purify with 25% ethyl acetate in hexanes to afford 0.45 g of the title compound.

PREPARATION 53

1-(3,5-Dichloro-4'-fluoro-biphenyl-4-ylmethyl)-3-(4-methoxy-cyclohexyl)-pyrrolidin-2-one A mixture of 1-(4-Bromo-2,6-dichloro-benzyl)-3-(4-methoxy-cyclohexyl)-pyrrolidin-2-one (0.4 g, 0.92 mmol) and 4-fluorophenylboronic acid (0.19 g, 1.38 mmol) in THF (15 mL) and water (5 mL) and sodium carbonate (0.29, 0.75 g) is purged with N₂. Treat the reaction with Pd(PPh₃)₄ (0.05 g, 0.046 mmol) and heat to 80° C. for 2 hour under N₂. Cool the reaction, dilute with ethyl acetate, and wash with HCl (1N) and water. Dry the organic layer (Na₂SO₄), remove the solvent in vacuo to afford crude product, and purify with a 35% ethyl acetate in hexanes to afford 0.45 g of the titled product. MS (m/z): 451 (M+).

EXAMPLE 1

3-Cyclohexyl-1-(2,6-dichloro-4-methoxy-benzyl)-pyrrolidin-2-one

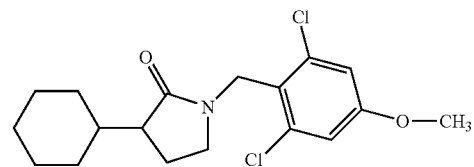

Treat a solution of 4-bromo-2-cyclohexyl-N-(2,6-dichloro-4-methoxy-benzyl)-butyramide (2.0 g, 4.6 mmol) in THF (30 mL) with diisopropyl ethyl amine (1.19 g, 9.19 mmol) at 40° C. for 12 hours and at reflux for 6 hours. Cool the reaction, dilute with ethylacetate and wash with HCl (1N) and water. After drying the organic layer over sodium sulfate, filtrate and concentrate under vacuum. Purify the residue by silica gel chromatography with 1:4 ethyl acetate:hexane to afford 1.3 g (80%) of the title compound. MS (m/z): 356 (M+).

EXAMPLE 2

3-Cyclohexyl-1-(2,6-dichloro-4-hydroxy-benzyl)-pyrrolidin-2-one

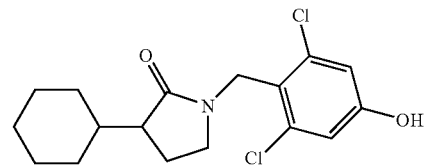

Treat a solution of 3-cyclohexyl-1-(2,6-dichloro-4-methoxy-benzyl)-pyrrolidin-2-one (1.3 g, 3.66 mmol) in dichloroethane (30 mL) at −20° C. with boron tribromide (1.0 M in DCM, 18.3 mL) for 2 hours. Warm the reaction up to room temperature and stir for 12 hours. Quench the reaction with methanol and remove the solvent under vacuum. Partition the residue with ethyl acetate and HCl (1 N). Wash the organic with water. After drying the organic layer, filtrate and concentrate to afford 1.2 g (99%) of the title compound. MS (m/z): 342 (M+).

EXAMPLE 3

3',5'-Dichloro-4'-(3-cyclohexyl-2-oxo-pyrrolidin-1-ylmethyl)-biphenyl-4-carboxylic acid methyl ester

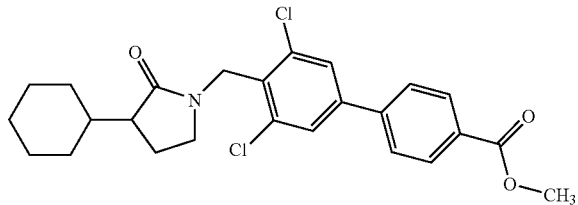

Bring a mixture of trifluoro-methanesulfonic acid 3,5-dichloro-4-(3-cyclohexyl-2-oxo-pyrrolidin-1-ylmethyl)-phenyl ester (0.80 g, 1.69 mmol), 4-methoxycarbonylphenylboronic acid (0.457 g, 2.53 mmol), sodium carbonate (0.538 g, 5.07 mmol) in THF (20 mL) and water (5 mL) to 60° C. To the mixture at 60° C., add $Pd(PPh_3)_4$ (0.098 g, 0.084 mmol), raise the reaction temperature to 80° C., and stir for 3 hours. Cool the reaction, dilute with ethyl acetate, and wash with water and brine. Dry the organic layer ($Na_2SO_4$), remove the solvent in vacuo to afford crude product, and purify on silica gel column with 20% ethyl acetate in hexanes to afford 0.62 g (80%) of the titled product. MS (m/z): 460 (M+).

EXAMPLE 4

3',5'-Dichloro-4'-(3-cyclohexyl-2-oxo-pyrrolidin-1-ylmethyl)-biphenyl-4-carboxylic acid

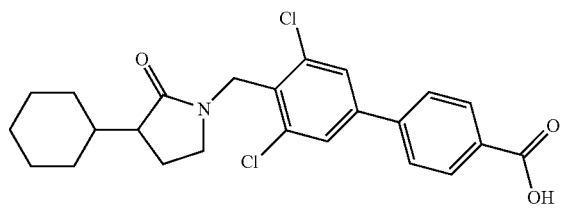

Treat a solution of 3',5'-dichloro-4'-(3-cyclohexyl-2-oxo-pyrrolidin-1-ylmethyl)-biphenyl-4-carboxylic acid methyl ester (0.6 g) in THF (15 mL) with 5N NaOH (5 mL) and stir at 50° C. for 12 hours. Quench the reaction with HCl (1N, 25 mL). Partition the mixture between ethyl acetate and water. Dry the organic layer ($Na_2SO_4$) and remove the solvent in vacuo to afford 0.56 g (96%) of the title compound. MS (m/z): 446 (M+).

EXAMPLE 5

3-Cyclohexyl-1-{3,5-dichloro-4'-[4-(2-fluoro-ethyl)-piperazine-1-carbonyl]-biphenyl-4-ylmethyl}-pyrrolidin-2-one

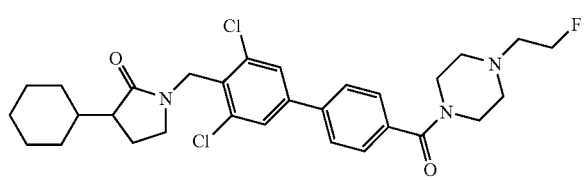

Dissolve 3',5'-dichloro-4'-(3-cyclohexyl-2-oxo-pyrrolidin-1-ylmethyl)-biphenyl-4-carboxylic acid (0.207 g, 0.465 mmol) in dichloromethane (15 mL) and add 1,1'-carbonyldiimidazole (0.151 g, 0.93 mmol). Stir under argon atmosphere at room temperature 1 hour then add N-2-fluoro-ethylpiperazine bistrifluoracetate (0.234 g, 0.651 mmol) and diisopropyl ethyl amine (0.168 g, 1.3 mmol). Stir 1 hour, dilute reaction with water, separate layers, and then wash sequentially with saturated sodium carbonate, water and brine. Collect the organic phase, dry over anhydrous magnesium sulfate and concentrate under reduced pressure. Purify via flash chromatography using 7% methanol in dichloromethane to afford 0.2 g (77%) of the title compound. MS (m/z): 560 (M+).

EXAMPLE 6

3-Cyclohexyl-1-[3,5-dichloro-4'-(4-isopropyl-piperazine-1-carbonyl)-biphenyl-4-ylmethyl]-pyrrolidin-2-one

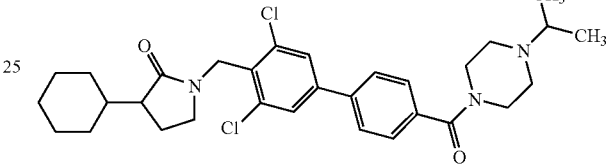

Prepare the title compound essentially as described by the procedure in Example 5. MS (m/z): 556 (M+).

EXAMPLE 7

3-Cyclohexyl-1-[3,5-dichloro-4'-(morpholine-4-carbonyl)-biphenyl-4-ylmethyl]-pyrrolidin-2-one

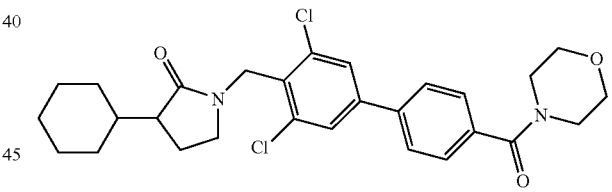

Prepare the title compound essentially as described by the procedure in Example 5. MS (m/z): 515 (M+).

PREPARATION 8a 3-Cyclohexyl-1-[3,5-dichloro-4'-(4-trifluoromethyl-piperidine-1-carbonyl)-biphenyl-4-ylmethyl]-pyrrolidin-2-one

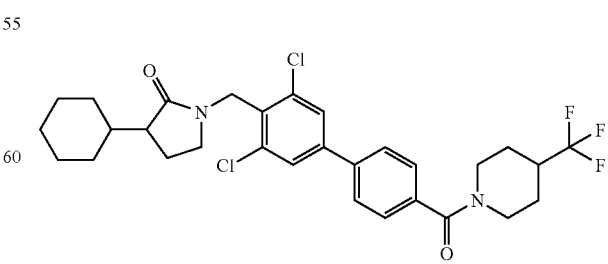

Prepare the title compound essentially as described by the procedure in Example 5. MS (m/z): 581 (M+).

PREPARATION 9a AND EXAMPLE 10

(R) and (S)-3-Cyclohexyl-1-{3,5-dichloro-4'-[4-(2-fluoro-ethyl)-piperazine-1-carbonyl]-biphenyl-4-ylmethyl}-pyrrolidin-2-one hydrochloride

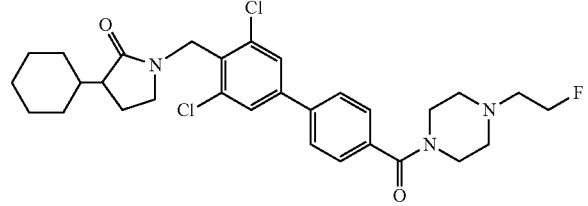

Separate racemic 3-cyclohexyl-1-{3,5-dichloro-4'-[4-(2-fluoro-ethyl)-piperazine-1-carbonyl]-biphenyl-4-ylmethyl}-pyrrolidin-2-one (Example 5) (0.224 g) into the enantiomers by chiral HPLC (Chiralcel OJ-H 4.6×150 mm column, isocratic 80:20 3A ethanol:acetonitrile with 0.2% dimethylethylamine, 0.6 mL/min, UV 260 nm) to afford 100 mg of enantiomer 1 (>99% ee, Ret.: 7.1 min.) and 95 mg of enantiomer 2 (98% ee, Ret.: 11.5 min.). Treat both enantiomers with HCl (1 N in ether) to afford the hydrochloride salt.

Enantiomer 1=Preparation 9a

Enantiomer 2=Example 10

EXAMPLE 11

1-[3,5-Dichloro-4'-(4-trifluoromethyl-piperidine-1-carbonyl)-biphenyl-4-ylmethyl]-3-(4-hydroxy-cyclohexyl)-pyrrolidin-2-one

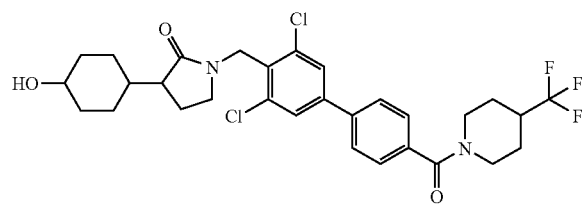

Treat a mixture of 3-[4-(tert-butyl-diphenyl-silanyloxy)-cyclohexyl]-1-[3,5-dichloro-4'-(4-trifluoromethyl-piperidine-1-carbonyl)-biphenyl-4-ylmethyl]-pyrrolidin-2-one (0.18 g), THF (6 mL) and water (6 mL) with TFA (2 mL) at room temperature for 1 hour and then at 55° C. for 12 hours. Cool the reaction, dilute with ethyl acetate, and wash with sodium bicarbonate (sat.). Dry the organic layer (Na$_2$SO$_4$), remove the solvent in vacuo to afford crude product, and purify on silica gel column with 50% ethyl acetate in hexanes to 100% ethyl acetate gradient to afford 0.075 g (59%) of the titled product. MS (m/z): 599 (M+).

PREPARATION 12a 1-(4-Bromo-2,6-dichloro-benzyl)-3-piperidin-1-yl-pyrrolidin-2-one Treat a solution of 3-piperidin-1-yl-pyrrolidin-2-one (0.33 g, 1.96 mmol) in DMF (6 mL) with 60% sodium hydride (0.12 g, 3.00 mmol) and stir at room temperature for 15 minutes under N$_2$. Cool the reaction to 0° C., treat with 5-bromo-2-(bromomethyl)-1,3-dichlorobenzene (0.70 g, 2.19 mmol), stir for 15 minutes at 0° C., warm to room temperature, and stir for 3 hours under N$_2$. Quench the reaction with water and dilute with diethyl ether. Dry the organic layer (Na$_2$SO$_4$), remove the solvent in vacuo to afford crude product, and purify with a 0 to 5% methanol in CH$_2$Cl$_2$ gradient to afford 0.718 g (90%) of the titled product. R$_f$=0.29 (9/1 CH$_2$Cl$_2$/methanol). ES MS (m/z): 407 (M+).

PREPARATION 13a 1-(3,5-Dichloro-4'-fluoro-biphenyl-4-ylmethyl)-3-piperidin-1-yl-pyrrolidin-2-one Purge a mixture of 1-(4-bromo-2,6-dichloro-benzyl)-3-piperidin-1-yl-pyrrolidin-2-one (0.150 g, 0.37 mmol) and 4-fluorophenylboronic acid (0.150 g, 1.07 mmol) in toluene (7 mL) and 2M sodium carbonate (1.3 mL) with N$_2$. Treat the reaction with Pd(PPh$_3$)$_4$ (0.043 g, 0.037 mmol) and heat to 90° C. for 4 hours under N$_2$. Cool the reaction, dilute with ethyl acetate, and wash with and water. Dry the organic layer (Na$_2$SO$_4$), remove the solvent in vacuo to afford crude product, and purify with a 0 to 10% methanol in CH$_2$Cl$_2$ gradient to afford 0.050 g (32%) of the titled product. R$_f$=0.46 (9/1 CH$_2$Cl$_2$/methanol). ES MS (m/z): 421 (M+).

EXAMPLE 14

3',5'-Dichloro-4'-(2-oxo-3-piperidin-1-yl-pyrrolidin-1-ylmethyl)-biphenyl-4-carboxylic acid methyl ester Purge a mixture of 1-(4-bromo-2,6-dichloro-benzyl)-3-piperidin-1-yl-pyrrolidin-2-one (0.429 g, 1.06 mmol) and 4-methoxycarbonyl phenylboronic acid (0.57 g, 3.16 mmol) in toluene (15 mL) and 2M sodium carbonate (3.7 mL) with $N_2$. Treat the reaction with $Pd(PPh_3)_4$ (0.061 g, 0.053 mmol) and heat to 90° C. for 7 hours under $N_2$. Cool the reaction, dilute with ethyl acetate, and wash with water. Dry the organic layer ($Na_2SO_4$), remove the solvent in vacuo afford crude product, and purify with a 0 to 10% methanol in $CH_2Cl_2$ gradient to afford 0.19 g (39%) of the titled product. $R_f$=0.40 (9/1 $CH_2Cl_2$/methanol). ES MS (m/z): 461 (M+).

PREPARATION 15a

3',5'-Dichloro-4'-(2-oxo-3-piperidin-1-yl-pyrrolidin-1-ylmethyl)-biphenyl-4-carboxylic acid

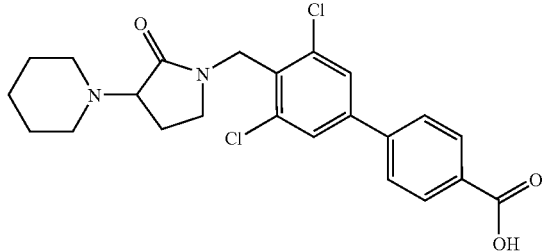

Treat a solution of 3',5'-Dichloro-4'-(2-oxo-3-piperidin-1-yl-pyrrolidin-1-ylmethyl)-biphenyl-4-carboxylic acid methyl ester (0.190 g, 0.41 mmol) in methanol (15 mL) with 5N NaOH (0.82 mL), heat to reflux, and cool and stir at room temperature for 16 hours. Remove the solvent in vacuo to give a residue and neutralize with 1N HCl. Dilute the mixture with ethyl acetate and wash with water. Dry the organic layer ($Na_2SO_4$), remove the solvent in vacuo to afford crude product, purify with a 0 to 10% methanol in $CH_2Cl_2$ gradient to afford 0.106 g (58%) of the titled product. $R_f$=0.50 (4/1 $CH_2Cl_2$/methanol). ES MS (m/z): 447 (M+).

EXAMPLE 16

1-[3,5-Dichloro-4'-(4-trifluoromethyl-piperidine-1-carbonyl)-biphenyl-4-ylmethyl]-3-piperidin-1-yl-pyrrolidin-2-one

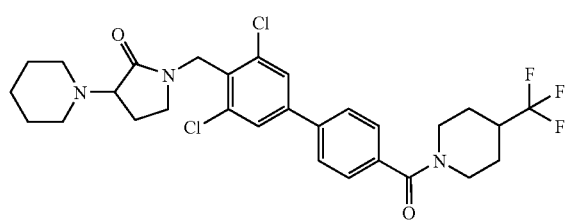

Treat a solution of Preparation 15a (0.097 g, 0.22 mmol) in $CH_2Cl_2$ (8 mL) with 1,1'-carbonyldiimidazole (0.056 g, 0.34 mmol) and stir for 1 hour at room temperature under $N_2$. Treat the reaction with 4-(trifluoromethyl)piperidine HCl (0.058 g, 0.31 mmol) and diisopropylethylamine (0.059 g, 0.46 mmol) and stir for 16 hours at room temperature under $N_2$. Dilute the reaction with water and extract with $CH_2Cl_2$. Dry the organic layer ($Na_2SO_4$), remove the solvent in vacuo to afford crude product, and purify on silica with a 0 to 10% methanol in $CH_2Cl_2$ gradient to afford 0.092 g (73%) of the titled product. $R_f$=0.50 (9/1 $CH_2Cl_2$/methanol). ES MS (m/z): 582 (M+).

EXAMPLE 17 AND PREPARATION 18A (R) and (S)-1-[3,5-Dichloro-4'-(4-trifluoromethyl-piperidine-1-carbonyl)-biphenyl-4-ylmethyl]-3-piperidin-1-yl-pyrrolidin-2-one

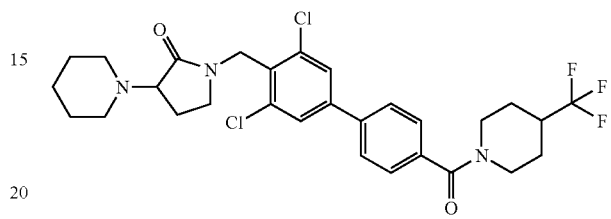

Separate racemic 1-[3,5-dichloro-4'-(4-trifluoromethyl-piperidine-1-carbonyl)-biphenyl-4-ylmethyl]-3-piperidin-1-yl-pyrrolidin-2-one into the enantiomers by chiral HPLC (Chiralpak AD 8×33 cm column, isocratic 50:50 3A ethanol:acetonitrile with 0.2% dimethylethylamine, 375 mL/min, UV 260 nm) to afford 36 mg of enantiomer 1 (98.4% ee) and 39 mg of enantiomer 2 (98.4% ee). Analytical HPLC: Chiralpak AD-H 4.6×150 mm column, isocratic 50:50 3A ethanol:acetonitrile with 0.2% dimethylethylamine, 0.6 mL/min, UV 260 nm.

Example 17=enantiomer 1 elutes 5.1 minutes. ES MS (m/z): 582 (M+).

Preparation 18a=enantiomer 2 elutes 6.5 minutes. ES MS (m/z): 582 (M+).

PREPARATION 19a 1-(4-Benzyloxy-2,6-dichloro-benzyl)-3-piperidin-1-yl-pyrrolidin-2-one

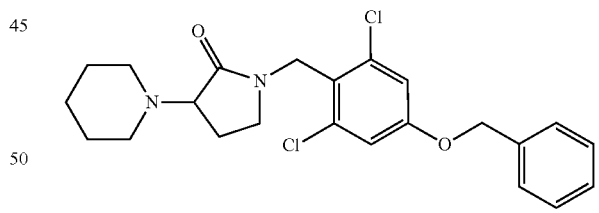

Treat a solution of 3-piperidin-1-yl-pyrrolidin-2-one (3.34 g, 19.8 mmol) in DMF (35 mL) with 60% sodium hydride (1.19 g, 29.8 mmol) and stir at room temperature for 15 minutes under $N_2$. Cool the reaction to 0° C., treat with 2-bromomethyl-1,3-dichloro-5-benzyloxy-benzene (7.56 g, 21.8 mmol), stir for 15 minutes at 0° C., warm to room temperature, and stir for 3 hours under $N_2$. Quench the reaction with water and extract with diethyl ether. Dry the organic layer ($Na_2SO_4$), remove the solvent in vacuo to afford crude product, and purify on silica with a 0 to 10% methanol in $CH_2Cl_2$ gradient to afford 8.01 g (93%) product. Purify the product further by trituration with diethyl ether to give 5.78 g (67%) of the titled product. $R_f$=0.48 (9/1 $CH_2Cl_2$/methanol). ES MS (m/z): 433 (M+).

PREPARATION 20a 1-(4-Benzyloxy-2,6-dichloro-benzyl)-3-(4,4-difluoro-piperidin-1-yl)-pyrrolidin-2-one

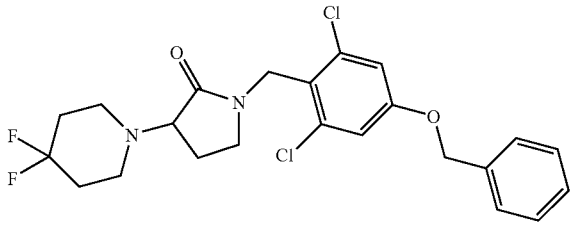

Prepare the titled product from (4,4-difluoro-piperidin-1-yl)-acetic acid methyl ester according to the procedure utilized to prepare Preparation 19a to afford 3.25 g of the titled product. $R_f$=0.22 (1:1 ethyl acetate:hexane). MS (m/z): 469 (M+).

PREPARATION 21a

1-[3,5-Dichloro-4'-(4-trifluoromethyl-piperidine-1-carbonyl)-biphenyl-4-ylmethyl]-3-(4-hydroxy-piperidin-1-yl)-pyrrolidin-2-one

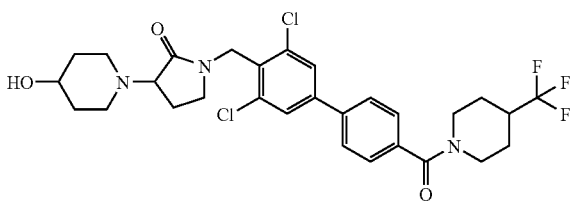

Treat a mixture of 3-[4-(tert-butyl-diphenyl-silanyloxy)-piperidin-1-yl]-1-[3,5-dichloro-4'-(4-trifluoromethyl-piperidine-1-carbonyl)-biphenyl-4-ylmethyl]-pyrrolidin-2-one (0.25 g, 0.299 mmol) in THF (10 mL) and water (5 mL) with trifluoroacetic acid (5 mL), heat to reflux, and stir for 4 hours under $N_2$. Cool the reaction and basify with 5N NaOH. Dilute the mixture with ethyl acetate and wash with water. Dry the organic layer ($Na_2SO_4$) and remove the solvent in vacuo to afford crude product. Purify with a 5 to 10% methanol in $CH_2Cl_2$ gradient to afford 0.078 g (44%) of the titled product. $R_f$=0.34 (9/1 $CH_2Cl_2$/methanol). ES MS (m/z): 598 (M+).

EXAMPLE 22

1-[3,5-Dichloro-4'-(4-trifluoromethyl-piperidine-1-carbonyl)-biphenyl-4-ylmethyl]-3-(4-fluoro-piperidin-1-yl)-pyrrolidin-2-one

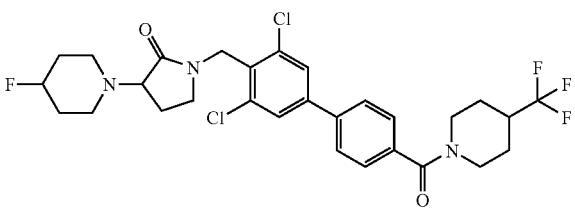

Treat a 0° C. solution of 1-[3,5-dichloro-4'-(4-trifluoromethyl-piperidine-1-carbonyl)-biphenyl-4-ylmethyl]-3-(4-hydroxy-piperidin-1-yl)-pyrrolidin-2-one (0.090 g, 0.15 mmol) in $CH_2Cl_2$ (5 mL) with (diethylamino)sulfur trifluoride (0.049 g, 0.305 mmol) and stir for 1 hour at 0° C. under $N_2$. Quench the reaction with saturated $NaHCO_3$, dilute with ethyl acetate, and wash with water. Dry the organic layer ($Na_2SO_4$), remove the solvent in vacuo to afford crude product, and purify with a 0 to 10% methanol in $CH_2Cl_2$ gradient to afford 0.019 g (85%) of the titled product. $R_f$=0.56 (9/1 $CH_2Cl_2$/methanol). ES MS (m/z): 600 (M+).

EXAMPLE 23

1-(3,5-Dichloro-[1,1'; 4', 1''']terphenyl-4-ylmethyl)-3-(4,4-difluoro-piperidin-1-yl)-pyrrolidin-2-one

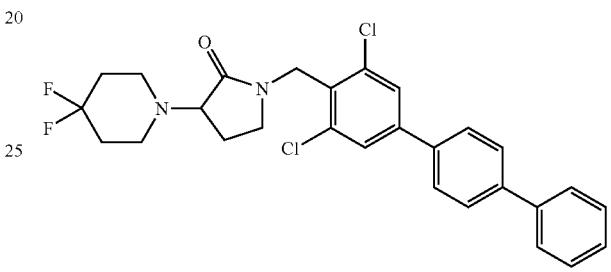

Purge with $N_2$ a mixture of trifluoro-methanesulfonic acid 3,5-dichloro-4-[3-(4,4-difluoro-piperidin-1-yl)-2-oxo-pyrrolidin-1-ylmethyl]-phenyl ester (0.097 g, 0.19 mmol), 4-biphenylboronic acid (0.045 g, 0.23 mmol) in THF (5 mL), and 2M sodium carbonate (0.29 mL). Treat the reaction with $Pd(PPh_3)_4$ (0.011 g, 0.01 mmol) and heat to 80° C. for 1 hour under $N_2$. Cool the reaction, dilute with ethyl acetate, and wash with water. Dry the organic layer with $Na_2SO_4$ and remove the solvent in vacuo to afford crude product. Purify on silica with 100% ethyl acetate to afford 0.098 g (100%) of the titled product. $R_f$=0.44 (100% ethyl acetate). MS (m/z): 515 (M+).

EXAMPLE 24

1-[3,5-Dichloro-4'-(4-carboxylic acid methyl ester)-biphenyl-4-ylmethyl]-3-(4,4-difluoro-piperidin-1-yl)-pyrrolidin-2-one

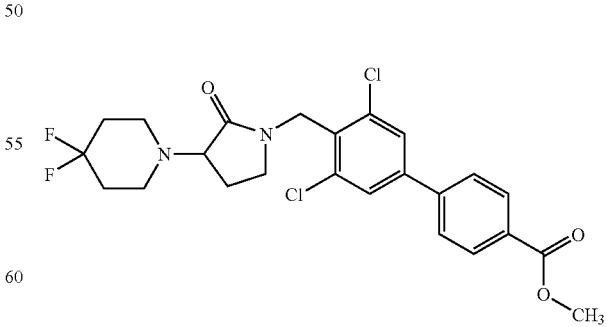

Purge with $N_2$ a mixture of trifluoro-methanesulfonic acid 3,5-dichloro-4-[3-(4,4-difluoro-piperidin-1-yl)-2-oxo-pyrrolidin-1-ylmethyl]-phenyl ester (1.13 g, 2.21 mmol), 4-methoxycarbonyl phenylboronic acid (0.48 g, 2.67 mmol)

in THF (35 mL) and 2M sodium carbonate (3.32 mL). Treat the reaction with Pd(PPh$_3$)$_4$ (0.125 g, 0.108 mmol) and heat to 80° C. for 1 hour under N$_2$. Cool the reaction, dilute with ethyl acetate, and wash with water. Dry the organic layer with Na$_2$SO$_4$ and remove the solvent in vacuo to afford crude product. Purify on silica with a 20 to 100% ethyl acetate in hexanes gradient to afford 1.06 g (97%) of the titled product. R$_f$=0.34 (100% ethyl acetate). MS (m/z): 497 (M+).

EXAMPLE 25

1-[3,5-Dichloro-4'-(4-trifluoromethyl-piperidine-1-carbonyl)-biphenyl-4-ylmethyl]-3-(4,4-difluoro-piperidin-1-yl)-pyrrolidin-2-one

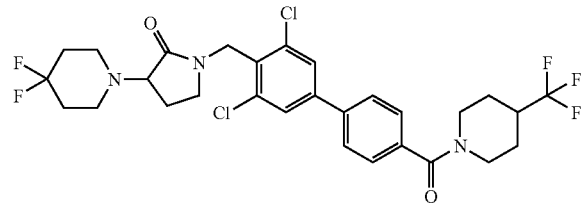

Treat a solution of 1-[3,5-dichloro-4'-(4-carboxylic acid)-biphenyl-4-ylmethyl]-3-(4,4-difluoro-piperidin-1-yl)-pyrrolidin-2-one (0.11 g, 0.22 mmol) in CH$_2$Cl$_2$ (7 mL) 1,1'-carbonyldiimidazole (0.073 g, 0.45 mmol) and stir for 2 hours at room temperature under N$_2$. Then, treat the reaction with 4-(trifluoromethyl)piperidine HCl (0.071 g, 0.68 mmol) and diisopropylethylamine (0.085 g, 0.66 mmol) and stir for 6 hours at room temperature under N$_2$. Dilute the reaction with ethyl acetate and wash with water. Dry the organic layer with Na$_2$SO$_4$ and remove the solvent in vacuo to afford crude product. Purify on silca with a 100% ethyl acetate and then by HPLC to afford 0.051 g (38%) of the titled product. R$_f$=0.35 (100% ethyl acetate). ES MS (m/z): 618 (M+).

EXAMPLE 26

3-(4-Bromo-cyclohexyl)-1-(3,5-dichloro-4'-fluoro-biphenyl-4-ylmethyl)-pyrrolidin-2-one

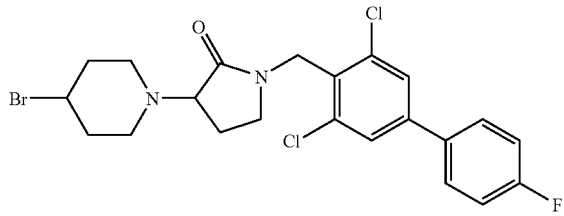

Treat a mixture 1-(3,5-Dichloro-4'-fluoro-biphenyl-4-ylmethyl)-3-(4-methoxy-cyclohexyl)-pyrrolidin-2-one (0.45 g, 1.0 mmol) in DCE (20 mL) with borontribromide at −20° C. for 2 hour under nitrogen. Slowly warm the reaction to room temperature and stir for 12 hours. Quench the reaction with methanol and concentrate. Purify the crude product on silica gel column with 25 to 50% ethyl acetate in hexanes gradient to afford 0.096 g of the titled product. MS (m/z): 499 (M+).

In the following section enzyme and functional assays are described which are useful for evaluating the compounds of the invention.

11β-HSD type 1 Enzyme Assay

Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 µL/well capacity) in the following fashion: 9 µL/well of substrate (2.22 mM NADP, 55.5 µM Cortisol, 10 mM Tris, 0.25% Prionex, 0.1% Triton X100), 3 µL/well of water to compound wells or 3 µL to control and standard wells, 6 µL/well recombinant human 11β-HSD type 1 enzyme, 2 µL/well of compound dilutions. For ultimate calculation of percent inhibition, a series of wells are added that represent assay minimum and maximum: one set containing substrate with 667 µM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes each plate individually from the stacker and places them in position for addition of 5 µL/well of a 250 µM carbenoxolone solution to stop the enzymatic reaction. Plates are then shaken once more for 15 seconds then placed into an Ultra 384 microplate reader (355EX/460EM) for detection of NADPH fluorescence.

Compounds of the invention can also tested for selectivity against 11-βHSD2 in an assay similar to that described for 11-βHSD1, but using the 11-βHSD2 enzyme. The assay using the 11-βHSD2 enzyme can be carried out by the methods described herein and supplemented by methods known in the art.

Human Aortic Smooth Muscle Cell Assay

Primary human aortic smooth muscle cells (AoSMC) are cultured in 5% FBS growth medium to a passage number of 6, then pelleted by centrifugation and resuspended at a density of 9×10$^4$ cells/mL in 0.5% FBS assay medium containing 12 ng/mL hTNFα to induce expression of 11β-HSD1. Cells are seeded into 96-well tissue culture assay plates at 100 µL/well (9×10$^3$ cells/well) and incubated for 48 hours at 37° C., 5% CO$_2$. Following induction, cells are incubated for 4 hours at 37° C., 5% CO$_2$ in assay medium containing test compounds then treated with 10 µL/well of 10 µM cortisone solubilized in assay medium, and incubated for 16 hours at 37° C., 5% CO$_2$. Medium from each well is transferred to a plate for subsequent analysis of cortisol using a competitive fluorescence resonance time resolved immunoassay. In solution, an allophycocyanin (APC)-cortisol conjugate and free cortisol analyte compete for binding to a mouse anti-cortisol antibody/Europium (Eu)-anti mouse IgG complex. Higher levels of free cortisol result in diminishing energy transfer from the Europium-IgG to the APC-cortisol complex resulting in less APC fluorescence. Fluorescent intensities for Europium and APC are measured using a LJL Analyst AD. Europium and APC excitation is measured using 360 nm excitation and 615 nm and 650 nm emission filters respectively. Time resolved parameters for Europuium were 1000 μs integration time with a 200 μs delay. APC parameters are set at 150 μs integration time with a 50 μs delay. Fluorescent intensities measured for APC are modified by dividing by the Eu fluorescence (APC/Eu). This ratio is then used to determine the unknown cortisol concentration by interpolation using a cortisol standard curve fitted with a 4-parameter logistic equation. These concentrations are then used to determine compound activity by plotting concentration versus % inhibition, fitting with a 4-parameter curve and reporting the $IC_{50}$.

All of the examples disclosed herein demonstrate activity in the human aortic smooth muscle cell assay with $IC_{50}$ of less than 500 nM. Preferred examples disclosed herein demonstrate activity in the human aortic smooth muscle cell assay with $IC_{50}$ of less than 300 nM. Data for example compounds in the human aortic smooth muscle cell assay are shown below:

average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 μl per animal, followed by a subcutaneous dose, 200 μl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum transferred to wells of 96-well plates (Corning Inc, Costar #4410, cluster tubes, 1.2 ml, polypropylene), and the plates are frozen at −20° C. until analysis by LC-MS/MS. For analysis, serum samples are thawed and the proteins are precipitated by the addition of acetonitrile containing d4-cortisol internal standard. Samples are vortex mixed and centrifuged.

| Example | Structure | $IC_{50}$ (nM) |
|---|---|---|
| 5 | [structure] | 15.4 |
| 16 | [structure] | 294 |

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male C57BL/6 mice are obtained from Harlan Sprague Dawley at The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer.

Data for example compounds in the acute in vivo cortisone conversion assay are shown below:

| Example | Structure | % Inhibition after 16 hours |
|---|---|---|
| 5 | [structure] | 84 (dose of 30 (mg/kg)) |

| Example | Structure | % Inhibition after 16 hours |
|---|---|---|
| 16 | 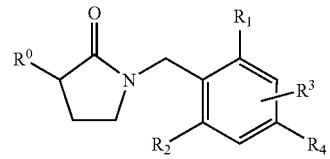 | 38 (dose of 10 (mg/kg)) |

Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/ Wiley-VCH, 2002); S. M. Berge, et al., "Pharmaceutical Salts," Journal of Pharmaceutical Sciences, Vol. 66, No. 1, January 1977. The compounds of the present invention are preferably formulated as pharmaceutical compositions administered by a variety of routes. Most preferably, such compositions are for oral administration. Such pharmaceutical compositions and processes for preparing same are well known in the art. See, e.g. REMINGTON: THE SCIENCE AND PRACTICE OF PHARMACY (A. Gennaro, et al., eds., 19th ed., Mack Publishing Co., 1995).

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from those described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intravenous, transdermal, intranasal, rectal, occular, topical, sublingual, buccal, or other routes. Oral administration may be preferred for treatment of the disorders described herein. In those instances where oral administration is impossible or not preferred, the composition may be made available in a form suitable for parenteral administration, e.g., intravenous, intraperitoneal or intramuscular.

What is claimed:
1. A compound structurally represented by the formula:

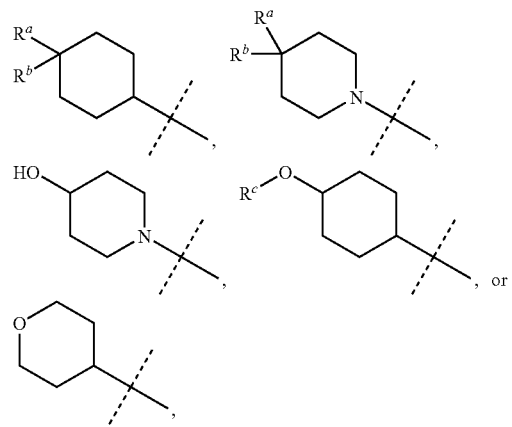

wherein
$R^0$ is wherein the dashed line represents the point of attachment to the $R^0$ position; wherein $R^a$ is —H or -halogen; $R^b$ is —H or halogen; $R^c$ is —H, —CH$_3$, or —CH$_2$—CH$_3$;
$R^1$ is —H, -halogen, —O—CH$_3$ (optionally substituted with one to three halogens), or —CH$_3$ (optionally substituted with one to three halogens);
$R^2$ is —H, -halogen, —O—CH$_3$ (optionally substituted with one to three halogens), or —CH$_3$ (optionally substituted with one to three halogens);
$R^3$ is —H or -halogen;
$R^4$ is
—OH, -halogen, -cyano, —(C$_1$-C$_4$)alkyl(optionally substituted with one to three halogens), —(C$_1$-C$_6$) alkoxy(optionally substituted with one to three halogens), —SCF$_3$, —C(O)O(C$_1$-C$_4$)alkyl, —O—CH$_2$—C(O)NH$_2$, —(C$_3$-C$_8$)cycloalkyl, —O-phenyl-C(O) O—(C$_1$-C$_4$)alkyl, —CH$_2$-phenyl, —NHSO$_2$—(C$_1$-C$_4$)alkyl, —NHSO$_2$-phenyl(R$^{21}$)(R$^{21}$), —(C$_1$-C$_4$) alkyl-C(O)N(R$^{10}$)(R11),

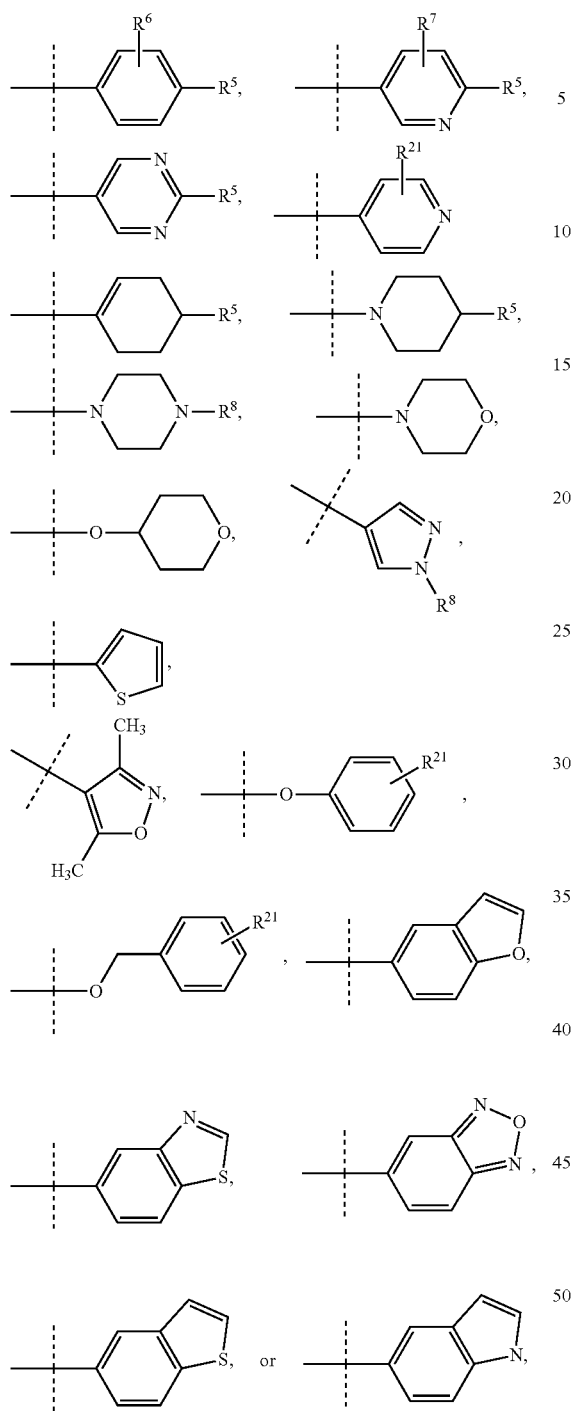

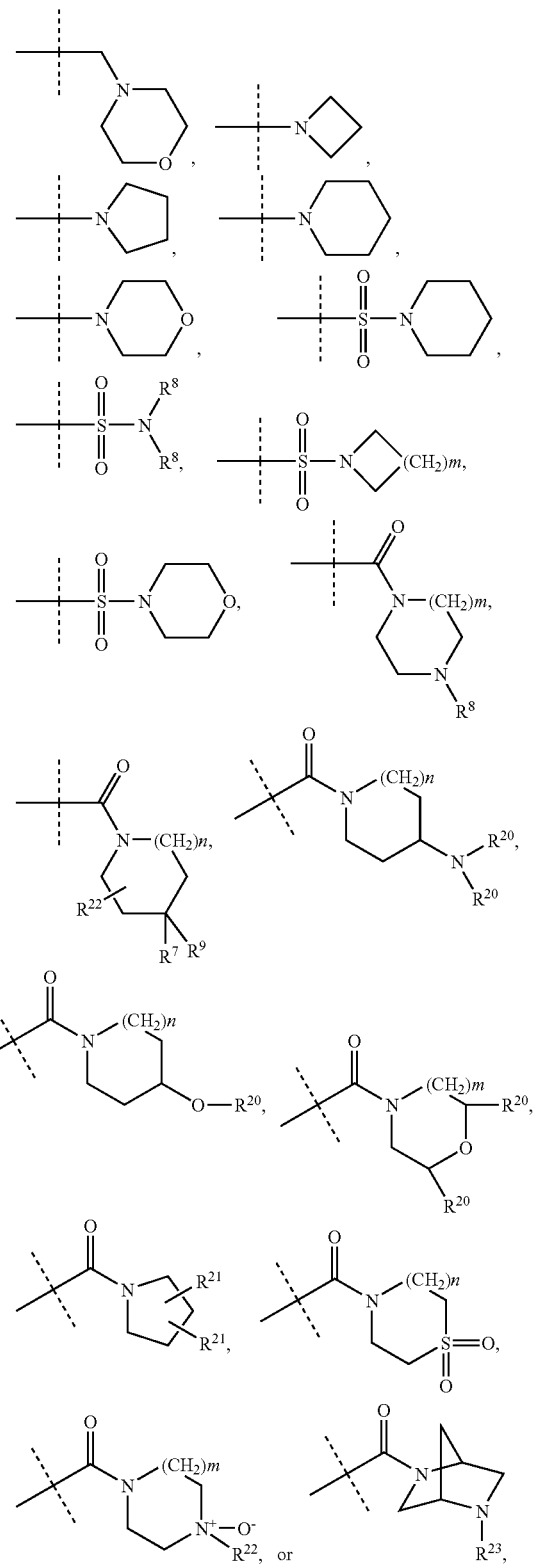

wherein the dashed line represents the point of attachment to the $R^4$ position;

$R^5$ is

—H, -halogen, —OH, —CN, —($C_1$-$C_4$)alkyl(optionally substituted with 1 to 3 halogens), —C(O)OH, —C(O)O—($C_1$-$C_4$)alkyl, —C(O)—($C_1$-$C_4$)alkyl, —O—($C_1$-$C_4$)alkyl(optionally substituted with 1 to 3 halogens), —$SO_2$—($C_1$-$C_4$)alkyl, —N($R^8$)($R^8$), -phenyl($R^{21}$)($R^{21}$), —C(O)—NH—($C_3$-$C_6$)cycloalkyl, wherein the dashed line represents the point of attachment to the position indicated by $R^5$;

wherein m is 1, 2, or 3;

wherein n is 0, 1, or 2, and wherein when n is 0, then "($CH_2$)n" is a bond;

$R^6$ is
—H, -halogen, —CN, or —($C_1$-$C_4$)alkyl(optionally substituted with 1 to 3 halogens);
$R^7$ is
—H, -halogen, or —($C_1$-$C_4$)alkyl(optionally substituted with 1 to 3 halogens);
$R^8$ is independently at each occurrence —H or —($C_1$-$C_6$) alkyl(optionally substituted with 1 to 3 halogens);
$R^9$ is —H or -halogen;
$R^{10}$ and $R^{11}$ are each independently
—H or —($C_1$-$C_4$)alkyl, or $R^{11}$ and $R^{12}$ taken together with the nitrogen to which they are attached form piperidinyl, piperazinyl, or pyrrolidinyl;
$R^{20}$ is independently at each occurrence —H, or —($C_1$-$C_3$) alkyl(optionally substituted with 1 to 3 halogens);
$R^{21}$ is independently at each occurrence —H, -halogen, or —($C_1$-$C_3$)alkyl(optionally substituted with 1 to 3 halogens);
$R^{22}$ is independently at each occurrence —H or —($C_1$-$C_6$) alkyl(optionally substituted with 1 to 3 halogens); and
$R^{23}$ is independently at each occurrence —H, —($C_1$-$C_4$) alkyl(optionally substituted with 1 to 3 halogens), or —C(O)O—($C_1$-$C_4$)alkyl,
or a pharmaceutically acceptable salt thereof.

2. A compound of claim 1 wherein $R^0$ is

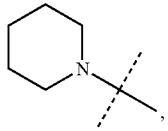

or a pharmaceutically acceptable salt thereof.

3. A compound of claim 1 wherein $R^0$ is

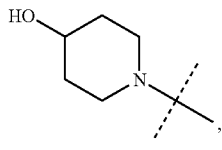

or a pharmaceutically acceptable salt thereof.

4. A compound of claim 1 wherein $R^0$ is

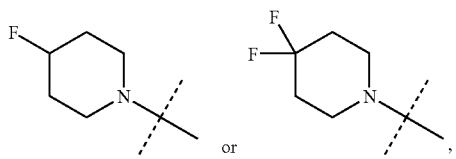

or a pharmaceutically acceptable salt thereof.

5. A compound of claim 1 wherein $R^0$ is

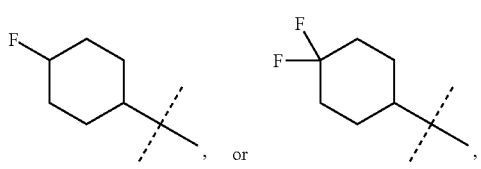

or a pharmaceutically acceptable salt thereof.

6. A compound of claim 1 wherein $R^0$ is

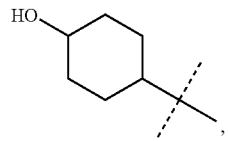

or a pharmaceutically acceptable salt thereof.

7. A compound of claim 1,
wherein $R^1$ is -chlorine and $R^2$ is -chlorine, and $R^3$ is —H, or a pharmaceutically acceptable salt thereof.

8. A compound of claim 7, wherein $R^4$ is

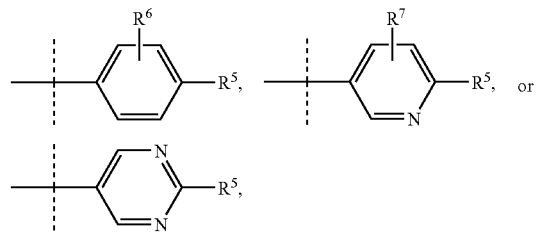

or a pharmaceutically acceptable salt thereof.

9. A compound claim 7 wherein $R^4$ is

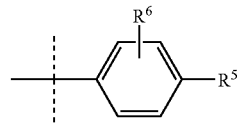

and $R^6$ is —H, or a pharmaceutically acceptable salt thereof.

10. A compound of claim 9 wherein $R^5$ is

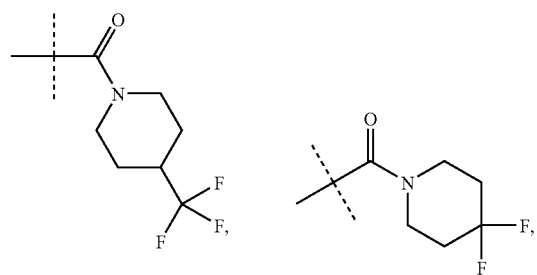

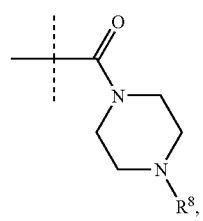

wherein R⁸ is —(C₁-C₃)alkyl (optionally substituted with 1 to 3 halogens), or

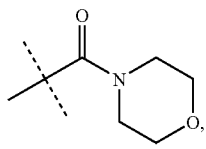

or a pharmaceutically acceptable salt thereof.

11. A compound of claim 9 wherein R⁵ is

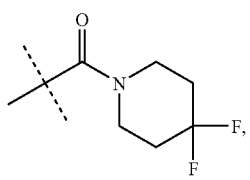

or a pharmaceutically acceptable salt thereof.

12. A compound claim 9 wherein R⁵ is

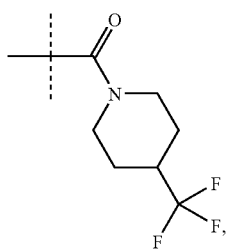

or a pharmaceutically acceptable salt thereof.

13. A compound of claim 9, wherein R⁵

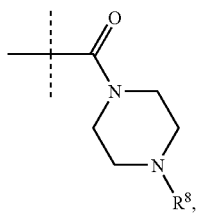

wherein R⁸ is —(C₁-C₃)alkyl (optionally substituted with 1 to 3 halogens), or a pharmaceutically acceptable salt thereof.

14. A compound of claim 9 wherein R⁵ is chlorine or fluorine, or a pharmaceutically acceptable salt thereof.

15. A compound that is 3-Cyclohexyl-1-{3,5-dichloro-4'-[4-(2-fluoro-ethyl)-piperazine-1-carbonyl]-biphenyl-4-ylmethyl}-pyrrolidin-2-one or a pharmaceutically acceptable salt thereof.

16. A compound that is 1-[3,5-Dichloro-4'-(4-trifluoromethyl-piperidine-1-carbonyl)-biphenyl-4-ylmethyl]-3-piperidin-1-yl-pyrrolidin-2-one or a pharmaceutically acceptable salt thereof.

17. A pharmaceutical composition which comprises a compound of claim 1, or a pharmaceutically acceptable salt thereof, and a pharmaceutically acceptable carrier.

18. A method for treating type 2 diabetes in a patient in need thereof which comprises administering to said patient an effective amount of a compound of claim 1, or a pharmaceutically acceptable salt thereof.

19. An intermediate for preparing a compound of claim 15 wherein the intermediate is

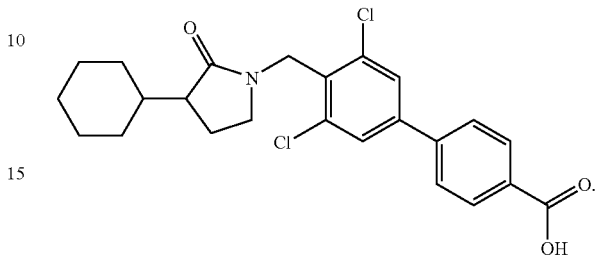

20. An intermediate for preparing a compound of claim 16 wherein the intermediate is

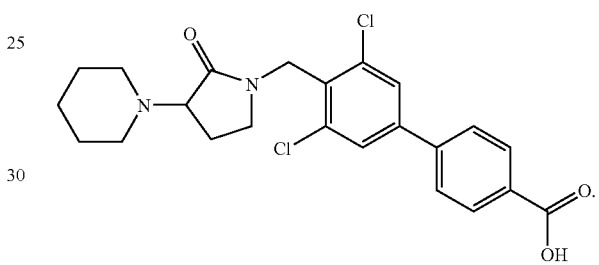

21. A compound of claim 1 selected from the group consisting of:
  3-Cyclohexyl-1-(2,6-dichloro-4-methoxy-benzyl)-pyrrolidin-2-one;
  3-Cyclohexyl-1-(2,6-dichloro-4-hydroxy-benzyl)-pyrrolidin-2-one;
  3',5'-Dichloro-4'-(3-cyclohexyl-2-oxo-pyrrolidin-1-ylmethyl)-biphenyl-4-carboxylic acid methyl ester;
  3',5'-Dichloro-4'-(3-cyclohexyl-2-oxo-pyrrolidin-1-ylmethyl)-biphenyl-4-carboxylic acid;
  3-Cyclohexyl-1-{3,5-dichloro-4'-[4-(2-fluoro-ethyl)-piperazine-1-carbonyl]-biphenyl-4-ylmethyl}-pyrrolidin-2-one;
  3-Cyclohexyl-1-[3,5-dichloro-4'-(4-isopropyl-piperazine-1-carbonyl)-biphenyl-4-ylmethyl]-pyrrolidin-2-one;
  3-Cyclohexyl-1-[3,5-dichloro-4'-(morpholine-4-carbonyl)-biphenyl-4-ylmethyl]-pyrrolidin-2-one;
  (R)-3-Cyclohexyl-1-{3,5-dichloro-4'-[4-(2-fluoro-ethyl)-piperazine-1-carbonyl]-biphenyl-4-ylmethyl}-pyrrolidin-2-one;
  (S)-3-Cyclohexyl-1-{3,5-dichloro-4'-[4-(2-fluoro-ethyl)-piperazine-1-carbonyl]-biphenyl-4-ylmethyl}-pyrrolidin-2-one;
  1-[3,5-Dichloro-4'-(4-trifluoromethyl-piperidine-1-carbonyl)-biphenyl-4-ylmethyl]-3-(4-hydroxy-cyclohexyl)-pyrrolidin-2-one;
  3',5'-Dichloro-4'-(2-oxo-3-piperidin-1-yl-pyrrolidin-1-ylmethyl)-biphenyl-4-carboxylic acid methyl ester;
  1-[3,5-Dichloro-4'-(4-trifluoromethyl-piperidine-1-carbonyl)-biphenyl-4-ylmethyl]-3-piperidin-1-yl-pyrrolidin-2-one;

(R)-1-[3,5-Dichloro-4'-(4-trifluoromethyl-piperidine-1-carbonyl)-biphenyl-4-ylmethyl]-3-piperidin-1-yl-pyrrolidin-2-one;

(S)-1-[3,5-Dichloro-4'-(4-trifluoromethyl-piperidine-1-carbonyl)-biphenyl-4-ylmethyl]-3-piperidin-1-yl-pyrrolidin-2-one;

1-[3,5-Dichloro-4'-(4-trifluoromethyl-piperidine-1-carbonyl)-biphenyl-4-ylmethyl]-3-(4-fluoro-piperidin-1-yl)-pyrrolidin-2-one;

1-(3,5-Dichloro-[1,1'; 4',1"]terphenyl-4-ylmethyl)-3-(4,4-difluoro-piperidin-1-yl)-pyrrolidin-2-one;

1-[3,5-Dichloro-4'-(4-carboxylic acid methyl ester)-biphenyl-4-ylmethyl]-3-(4,4-difluoro-piperidin-1-yl)-pyrrolidin-2-one;

1-[3,5-Dichloro-4'-(4-trifluoromethyl-piperidine-1-carbonyl)-biphenyl-4-ylmethyl]-3-(4,4-difluoro-piperidin-1-yl)-pyrrolidin-2-one; and 3-(4-Bromo-cyclohexyl)-1-(3,5-dichloro-4'-fluoro-biphenyl-4-ylmethyl)-pyrrolidin-2-one;

or a pharmaceutically acceptable salt thereof.

* * * * *